(12) United States Patent
Farco et al.

(10) Patent No.: US 9,301,865 B2
(45) Date of Patent: Apr. 5, 2016

(54) ACCESSORY ANCHORING SYSTEM AND METHOD

(71) Applicants: Lauren Marie Farco, Hoboken, NJ (US); Joseph Farco, Hoboken, NJ (US)

(72) Inventors: Lauren Marie Farco, Hoboken, NJ (US); Joseph Farco, Hoboken, NJ (US)

( * ) Notice: Subject to any disclaimer, the term of this patent is extended or adjusted under 35 U.S.C. 154(b) by 227 days.

(21) Appl. No.: 13/621,264

(22) Filed: Sep. 16, 2012

(65) Prior Publication Data
US 2014/0081191 A1    Mar. 20, 2014

(51) Int. Cl.
| | | |
|---|---|---|
| A44C 15/00 | (2006.01) | |
| A44C 9/00 | (2006.01) | |
| A44C 5/00 | (2006.01) | |
| A61F 5/01 | (2006.01) | |

(52) U.S. Cl.
CPC ............. *A61F 5/0118* (2013.01); *A44C 9/0084* (2013.01); *A44C 15/00* (2013.01); *A61F 5/0111* (2013.01)

(58) Field of Classification Search
USPC .................. 224/255, 268, 257, 908, 220, 219; 248/693, 690; 63/1.18, 1.11; 24/3.13, 24/3.1
See application file for complete search history.

(56) References Cited

U.S. PATENT DOCUMENTS

| | | | | |
|---|---|---|---|---|
| 417,569 | A | * | 12/1889 | Margileth ...................... 63/1.18 |
| 732,532 | A | * | 6/1903 | Fallek ................................ 63/15 |
| D67,909 | S | * | 7/1925 | Staub ................................ D11/2 |
| 1,628,278 | A | | 5/1927 | Scheuer |
| 1,691,445 | A | * | 11/1928 | Meliodon ...................... 63/1.18 |
| D145,318 | S | * | 7/1946 | Lowenst ........................... D11/2 |
| 2,522,719 | A | * | 9/1950 | Johnson ......................... 224/220 |
| 2,665,042 | A | * | 1/1954 | Starolis ......................... 224/255 |
| 3,656,244 | A | * | 4/1972 | Andrade ............................. 36/1 |
| 4,097,931 | A | | 7/1978 | Hirose |
| 4,121,360 | A | * | 10/1978 | Vlerebome ...................... 40/586 |
| 4,176,839 | A | | 12/1979 | Pinkus |
| D253,917 | S | * | 1/1980 | Wilkinson ..................... D2/896 |
| 4,215,556 | A | | 8/1980 | Mroz |
| 4,441,711 | A | | 4/1984 | Dubar |
| 4,479,648 | A | | 10/1984 | Alivo, Jr. |
| 4,756,453 | A | | 7/1988 | Pettit |
| 4,831,997 | A | | 5/1989 | Greene |
| 4,868,927 | A | | 9/1989 | Bourdeau |
| 4,915,272 | A | | 4/1990 | Vlock |
| 5,110,154 | A | | 5/1992 | Street |
| 5,195,188 | A | | 3/1993 | Bourdeau |
| 5,322,199 | A | | 6/1994 | White |
| 5,345,610 | A | | 9/1994 | Belanger |
| 5,386,710 | A | * | 2/1995 | Moore ................................ 63/3 |
| D357,641 | S | * | 4/1995 | Grodin ............................ D11/2 |
| 5,445,566 | A | | 8/1995 | Hayes |
| 5,466,215 | A | | 11/1995 | Lair et al. |
| 5,487,188 | A | | 1/1996 | Micheloni |
| 5,491,986 | A | | 2/1996 | White |
| 5,581,924 | A | | 12/1996 | Peterson |
| 5,658,353 | A | | 8/1997 | Layton |
| 5,671,481 | A | | 9/1997 | Giard |
| 5,673,826 | A | | 10/1997 | Stolk |

(Continued)

OTHER PUBLICATIONS

The Ashley Book of Knots ("ABOK") (Geoffrey Budworth, Ed. 1993), 185-197, 289-312, 335-336, 346-352, 597-605.

*Primary Examiner* — Jack W Lavinder

(57) ABSTRACT

An anchoring system has a brace configured to be worn on a human limb, an accessory configured to be worn on a human digit, and a harness coupling the accessory to the brace by a self-looping length of the harness comprising a portion of the harness most proximal to the brace and a portion of the harness most distal to the brace.

20 Claims, 17 Drawing Sheets

(56) References Cited

U.S. PATENT DOCUMENTS

| | | | |
|---|---|---|---|
| 5,729,831 A | 3/1998 | Kuhlmann | |
| 5,761,745 A | 6/1998 | Sato | |
| 5,785,217 A | 7/1998 | Gorham, Jr. | |
| 5,836,024 A | 11/1998 | Uglehus | |
| 5,887,282 A | 3/1999 | Lenhart | |
| 5,888,180 A | 3/1999 | Dewberry | |
| 5,899,369 A | 5/1999 | Macripo | |
| 5,922,336 A | 7/1999 | Tebbe | |
| 5,924,136 A | 7/1999 | Ogean | |
| 5,934,526 A | 8/1999 | Rosenbaum | |
| 5,946,728 A | 9/1999 | Tane | |
| 5,974,701 A | 11/1999 | Busch | |
| 6,094,747 A * | 8/2000 | Malick | 2/159 |
| 6,094,939 A | 8/2000 | Gavello | |
| D432,760 S * | 10/2000 | Brachfeld | D2/896 |
| 6,146,319 A | 11/2000 | Tarail | |
| 6,182,169 B1 * | 1/2001 | Force et al. | 710/62 |
| 6,272,688 B1 | 8/2001 | Wilson | |
| 6,360,684 B1 | 3/2002 | Quaglia | |
| 6,393,619 B1 * | 5/2002 | Bardes | 2/232 |
| 6,450,402 B1 | 9/2002 | Regev | |
| 6,473,906 B2 | 11/2002 | Kambe et al. | |
| 6,484,910 B1 | 11/2002 | Korkos | |
| 6,513,685 B1 * | 2/2003 | Tzoubris | 223/111 |
| D476,263 S | 6/2003 | Walters | |
| 6,687,916 B2 | 2/2004 | Thompson | |
| 6,715,152 B2 | 4/2004 | Mazzarolo | |
| 6,748,605 B1 | 6/2004 | Brinkmann | |
| 7,237,272 B2 | 7/2007 | Bötcher | |
| 7,305,718 B2 | 12/2007 | Avallone | |
| 7,371,472 B2 | 5/2008 | Fukuda | |
| D572,626 S | 7/2008 | Merriam-Smith | |
| D576,511 S * | 9/2008 | Cunningham | D11/8 |
| D603,293 S | 11/2009 | Merriam-Smith | |
| 7,694,352 B2 | 4/2010 | Kogawa et al. | |
| D616,790 S | 6/2010 | Mear | |
| 7,775,396 B2 | 8/2010 | Xu | |
| 7,797,758 B2 | 9/2010 | Keppler et al. | |
| 7,802,316 B2 | 9/2010 | Hofmann | |
| 7,845,020 B2 | 12/2010 | Jaunault et al. | |
| 7,938,811 B2 | 5/2011 | Furukawa | |
| 7,971,277 B2 | 7/2011 | Romiti | |
| 8,109,418 B1 | 2/2012 | Recchia | |
| 8,540,544 B1 | 9/2013 | Logue | |
| 2002/0056156 A1 | 5/2002 | Kambe et al. | |
| 2003/0172436 A1 | 9/2003 | Thompson | |
| 2005/0193468 A1 | 9/2005 | Chung | |
| 2006/0042313 A1 * | 3/2006 | Mattiacci | 63/1.18 |
| 2006/0048259 A1 | 3/2006 | Keppler | |
| 2006/0219741 A1 | 10/2006 | Clark | |
| 2006/0225253 A1 * | 10/2006 | Bates | 24/3.13 |
| 2007/0000017 A1 | 1/2007 | Hofmann | |
| 2007/0067964 A1 * | 3/2007 | McQuarrie | 24/3.13 |
| 2007/0226872 A1 | 10/2007 | Huh | |
| 2008/0000008 A1 | 1/2008 | Nagao et al. | |
| 2008/0000009 A1 | 1/2008 | Kogawa et al. | |
| 2008/0073388 A1 | 3/2008 | Saegusa | |
| 2008/0078010 A1 | 4/2008 | Micheloni | |
| 2008/0235846 A1 | 10/2008 | Schossberger | |
| 2009/0152312 A1 | 6/2009 | Li | |
| 2009/0242593 A1 | 10/2009 | Hildebrandt | |
| 2009/0276979 A1 * | 11/2009 | Kauffman et al. | 24/3.13 |
| 2010/0095427 A1 | 4/2010 | Romiti | |
| 2010/0147909 A1 | 6/2010 | Kelly et al. | |
| 2010/0275651 A1 * | 11/2010 | Wright | 63/15.6 |
| 2011/0005274 A1 | 1/2011 | Greubel et al. | |
| 2011/0016607 A1 | 1/2011 | Ashmore et al. | |
| 2011/0139834 A1 | 6/2011 | Joostberns | |
| 2011/0314866 A1 | 12/2011 | Niikura | |
| 2011/0315724 A1 | 12/2011 | Whitlaw | |
| 2012/0223109 A1 | 9/2012 | Wheeler, Sr. | |
| 2012/0263895 A1 | 10/2012 | Jeter, Jr. | |
| 2012/0273541 A1 * | 11/2012 | Zwach | 224/615 |
| 2012/0308443 A1 | 12/2012 | Tropper et al. | |
| 2013/0117987 A1 | 5/2013 | Rienecker | |
| 2013/0146042 A1 | 6/2013 | LoRocco et al. | |
| 2013/0167282 A1 | 7/2013 | Ramirez | |
| 2013/0326790 A1 | 12/2013 | Cauwels et al. | |
| 2014/0305974 A1 | 10/2014 | Purcel et al. | |

* cited by examiner

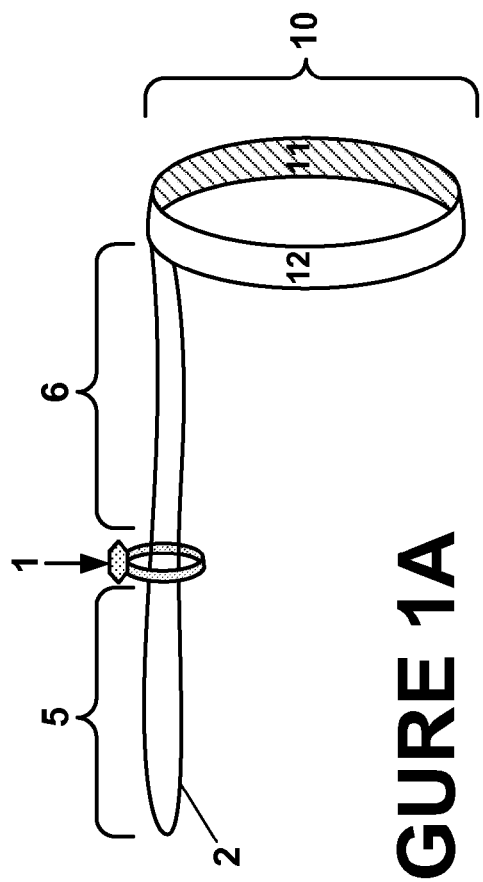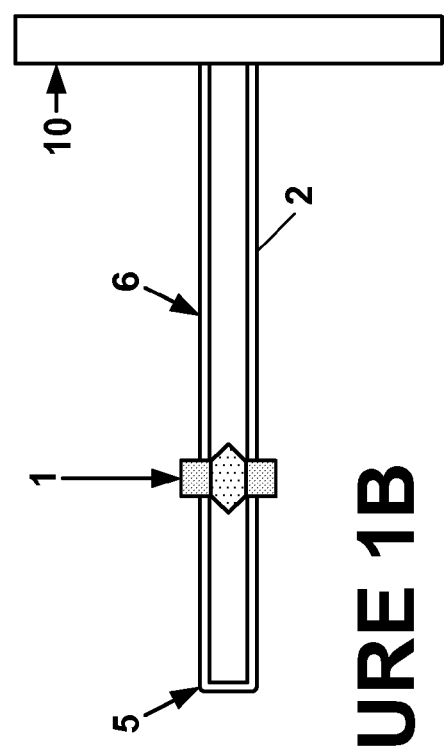

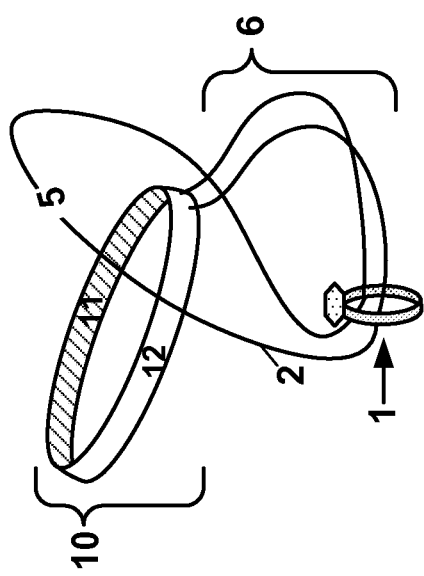
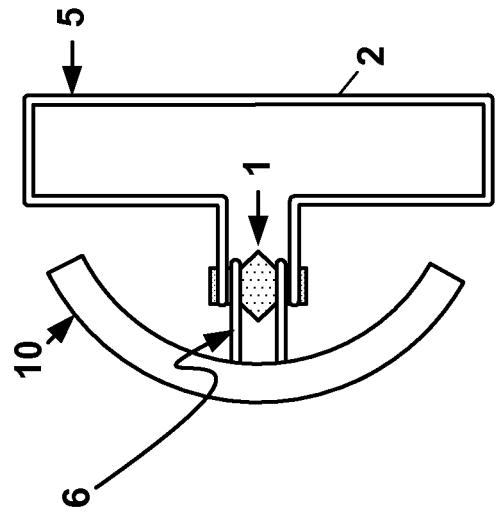
FIGURE 3A
FIGURE 3B

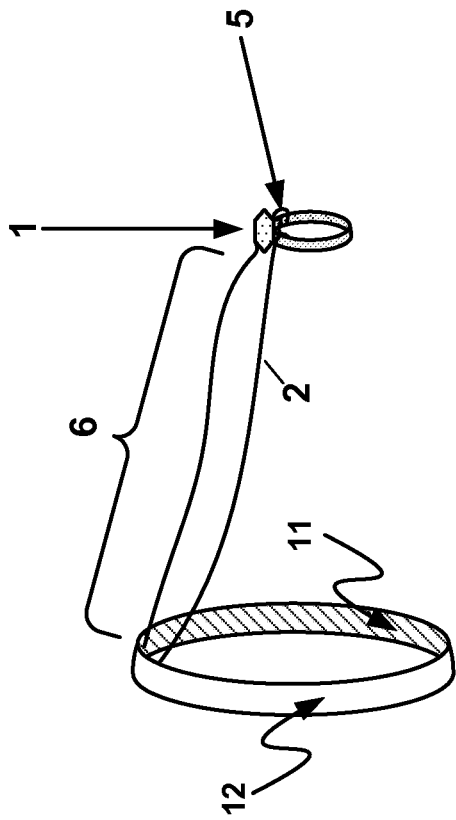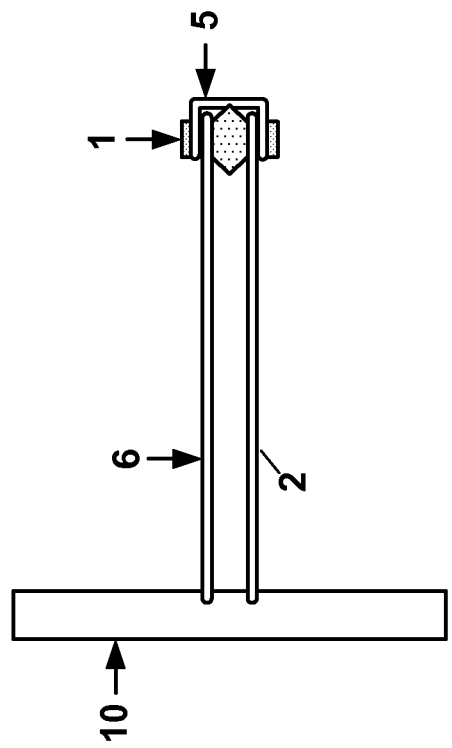
FIGURE 4A
FIGURE 4B

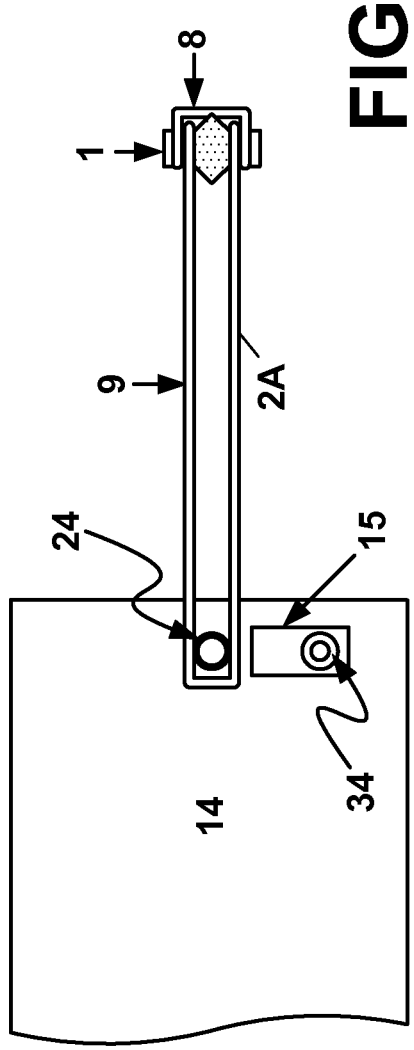
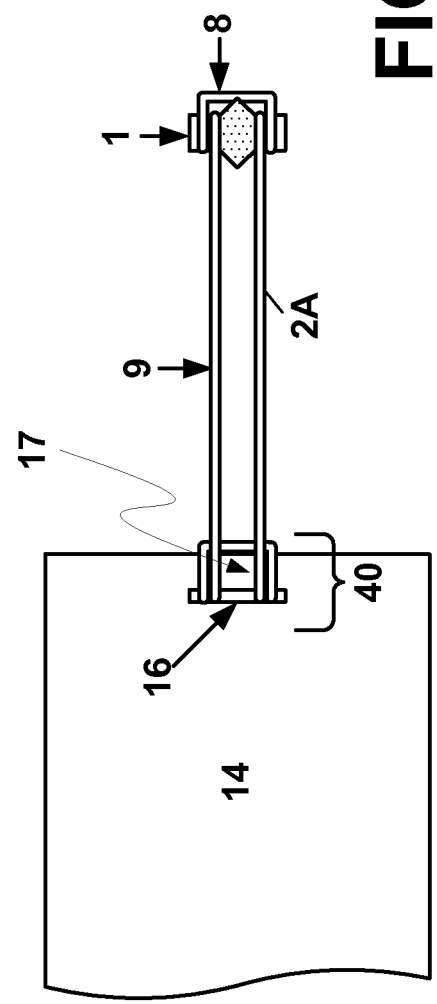

ACCESSORY ANCHORING SYSTEM AND METHOD

FIELD OF THE INVENTION

Disclosed are embodiments of the invention that relate to, among other things, assisting accessory wearers in limiting large displacements of their accessories while in motion.

BACKGROUND

A large amount of activity involves the use of hands and feet. The active digits of these appendages are in motion and experience vibrational, torsional, shock, and other disruptive forces.

The fingers of a hand experience a wide degree of movement and engage in a number of jostling motions. Accessories, such as rings or other jewelry, worn around a finger may be subject to forces that can cause displacement of the accessory and complete detachment of the accessory from the finger. For example, married women have been known to lose engagement rings due to routine activities in their lives.

The toes of a foot experience numerous shock forces and constant flexing when in use. Accessories, such as jewelry, worn around a toe may be subject to forces that can cause displacement of the accessory and, in certain instances, complete detachment of the accessory from the toe.

Many accessories adorning a finger or toe do not provide for ample attachments to other appendages of the body. Prior art options for coupling accessories from the wearer's finger or toe to the wearer's arms/wrists or legs/ankles, respectively, can be uncomfortable and there exists little motivation based on the prior art to attempt such coupling.

SUMMARY OF THE INVENTION

An exemplary anchoring system includes a brace that is capable of being worn on a human limb and a harness that couples to the brace. The harness couples an accessory that can be worn on a human digit by engaging the accessory in a self-looping configuration involving a portion of the harness that is closest to the brace and a portion of the harness that is the furthest from the brace.

An exemplary anchoring system may have a brace that is removable, is a piece of clothing, or can attach to a prosthetic. An exemplary brace can be worn on an arm, leg, wrist, or ankle. An exemplary accessory may be worn on a finger or toe.

An exemplary harness may be a single strand, an open loop, or a closed loop. An exemplary harness may have at least one hoop located about the harness, including on an intermediate portion of the harness or at either of its terminal ends. An exemplary harness may be disengaged from an exemplary brace or may be attached permanently.

An exemplary anchoring system may possess one or more charms on either of the brace or the harness. Further, an exemplary anchoring system may also include a signaling circuit to detect disengagement of the harness from the brace.

BRIEF DESCRIPTION OF THE DRAWINGS

FIGS. 1A and 1B illustrate an isometric and top plan view of an exemplary accessory anchor in an exemplary unwound state.

FIGS. 3A and 3B illustrate an isometric and top plan view of an exemplary accessory anchor in an exemplary winding action.

FIGS. 4A and 4B illustrate an isometric and top plan view of an exemplary accessory anchor in an exemplary wound state.

FIGS. 8A and 8B illustrate yet other exemplary wound states for an exemplary accessory anchor.

Figure 2A:
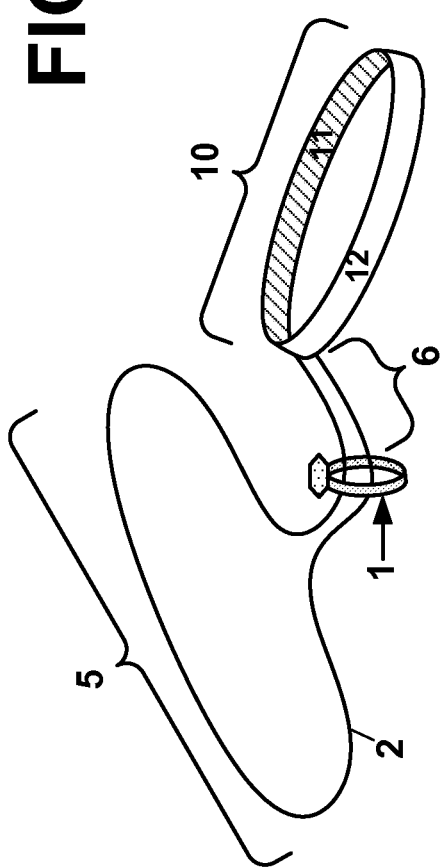
FIGS. 2A and 2B illustrate an isometric and top plan view of an exemplary accessory anchor prepared for an exemplary winding action.

In the drawings like characters of reference indicate corresponding parts in the different figures. The drawing figures, elements and other depictions should be understood as being interchangeable and may be combined in any like manner in accordance with the disclosures and objectives recited herein.

DETAILED DESCRIPTION

FIG. 1A illustrates an exemplary accessory anchor which comprises a brace 10 with an inner side 11 and an outer side 12. Connected to either of the inner side 11 or outer side 12 of brace 10 is a harness 2. In an exemplary embodiment, harness 2 passes through an opening in accessory 1. The section of harness 2 that passes through an exemplary accessory 1 is section 5 and the section of harness 2 that is closest to brace 10 is section 6.

An exemplary brace 10 may be composed of any suitable material for being worn by a user, such as any fabric, plastic, composite, metal, or other material that can be made to fit around an arm or leg. Preferably, brace 10 is made of cloth, plastic, or rubber similar to a bracelet or wrist band. Alternatively, brace 10 may be a component of another wearable device known to those skilled in the art, such as, for example, a watch, a bracelet, a medical cast, a prosthetic limb, or a piece of clothing, including a shirt sleeve or pant leg.

An exemplary harness 2 may be composed of any suitable material capable of achieving on or more of the following: being able to fit in, through or around an accessory 1, hold an accessory 1 to brace 10, or stay firmly attached to brace 10, for example. In an exemplary embodiment, harness 2 may be a loop of material or a single strand of material. Harness 2 may be a wire, a ribbon, a twine, a conductor of electricity or heat, a threaded material such as a threaded polymer or composite, a fabric such as cotton, nylon, Lycra, or yarn, a rubber or elastomer material, or any other suitable construct. In one embodiment, harness 2 may be able to hold onto an accessory 1 with minimal discomfort and friction to the area where the accessory is to be worn. Accordingly, harness 2 may be covered with or made of ePTFE or other breathable, non-reactive materials about its length or at the sections of accessory 1 attachment. In another embodiment, harness 2 may be configured to withstand the forces exerted on accessory 1 while worn by the user. Accordingly, harness 2 may be an interwoven fabric with sufficient tensile strength and light weight or an elastic material with a suitable modulus of elasticity. An exemplary harness 2 may be an elastomer-coated wire or a fiber-coated wire. In another exemplary embodiment, harness 2 may be a wire with differing cross-sectional areas. According to this exemplary embodiment, harness 2 may have a first cross section for attaching to brace 10, for example section 6, and a second cross section for holding accessory 1, for example section 5.

Brace 10 and harness 2 of an exemplary accessory anchor system may be coupled in any suitable way to hold accessory 1 on the user. Where brace 10 and harness 2 are made of the same type of material, such as a fabric or a plastic, they may be integrated as one piece. Alternatively, brace 10 and harness 2 may be bonded together, screwed into or between one another, clipped together, hooked around or in one another, epoxied to each other, sewed together, interwoven, clamped together, stitched on top of or inside one another, glued together, magnetically coupled to one another, looped about one another, or any other substantially equivalent coupling methods known to those skilled in the art. An exemplary connection between brace 10 and harness 2 may be capable of withstanding forces exerted on accessory 1 that might otherwise cause accessory 1 to detach from the digit.

An exemplary accessory 1 may be any object that can adorn the finger, hand, or toe of a user, prosthetic or otherwise. An exemplary accessory 1 may be a ring, a thimble, a guitar pick, a tool, a palm bracelet, nail ring, or any other accessory known to those skilled in the art which can be used in conjunction with the disclosures of the present invention.

FIGS. 1A and 1B illustrate an embodiment of an accessory anchor in an exemplary threading step of an exemplary accessory anchor method. Section 6 of harness 2 extends from any point on brace 10 capable of coupling a particular harness 2, for example, if harness 2 and the inner side 11 of brace 10 are made of the same material but differ from the material making up outer side 12 of brace 10, then harness 2 need not couple to outer side 12 of brace 10. A suitable harness 2 and brace 10 may be coupled at any point capable of operating according to the disclosures herein. In an exemplary threading step of an exemplary accessory anchoring method, section 5 of harness 2 passes underneath and through an accessory 1. Any length of harness 2 may make up sections 5 and 6 without regard to the operability of an exemplary accessory anchor. In an exemplary threading step, harness 2 section 5 may be greater in length than section 6. Alternatively, harness 2 section 5 may only be as long as to allow brace 10 to pass therebetween.

Figure 2B:
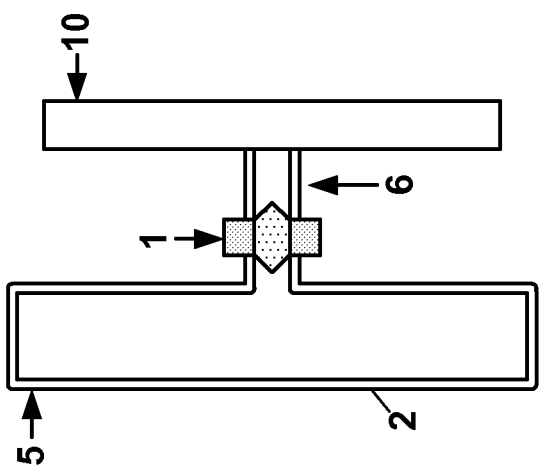

FIGS. 2A and 2B illustrate an exemplary expansion step in an exemplary accessory anchoring method. According to an exemplary embodiment, section 5 of harness 2 may increase in length compared to section 6. While illustrated as such in FIGS. 2A and 2B, section 5 may be the same or lesser length than section 6 depending on the shape and size of brace 10. For example, section 5 may be only long enough to allow brace 10 to pass between the spaces circumscribed by its surface. Alternatively, section 5 may be the same length as section 6. In embodiments where harness 2 is elastic, section 5 may be elastically deformed to a length capable of fitting the brace 10 through the spaces circumscribed by its surface. In an exemplary operation, the spaces between the surfaces of portion 5 that are most distal to brace 10 may expand while the spaces between the surfaces of portion 5 most proximal to accessory 1 may not substantially change.

FIGS. 3A and 3B illustrate an exemplary passing step of an exemplary accessory anchoring method. According to FIG. 3A, brace 10 of an exemplary accessory anchor may pass under and through the substantially arched portion of harness 2 section 5. In this exemplary embodiment, outside 12 of brace 10 may be compressed to fit brace 10 between the openings formed by the surfaces of section 5 of harness 2. An exemplary passing step of an exemplary accessory anchoring method may take place at any location about accessory 1.

FIG. 3B illustrates an exemplary passing step of an exemplary accessory anchoring method after brace 10 passes through the openings formed by the surfaces of section 5 of harness 2. According to the exemplary embodiment of FIG. 3B, brace 10 of an exemplary accessory anchor may be bent, compressed, folded, wrapped, rolled, or otherwise contorted to fit through the openings formed by surfaces of section 5. As an exemplary brace 10 passes through section 5 of harness 2, it also carriers through section 6. As depicted in the illustrative embodiment of FIG. 3B, section 6 may pass over the top of accessory 1 in one direction while section 5 passes over the top of accessory 1 in an opposite direction. While FIG. 3B illustrates the parts of section 5 and section 6 going across accessory 1 to be parallel and non-overlapping, sections of harness 2 may overlap, intersect, or otherwise engage each other as part of an exemplary passing step of an exemplary accessory anchoring method.

FIG. 4A illustrates an exemplary loop step of an exemplary accessory anchoring method. Harness 2 of an exemplary accessory anchor may be located about accessory 1. According to the illustrated exemplary loop step, section 6 may be substantially the entire length of harness 2 and section 5 may make up substantially the length of harness 2 most engaged with the surfaces of accessory 1. In another view of the exemplary embodiment of FIG. 4A, FIG. 4B illustrates an exemplary accessory anchor in an exemplary anchoring mode. As illustrated, accessory 1 may be held in place by the interloopings of harness 2 around its surface. According to one embodiment as illustrated by FIG. 4B, section 5 of harness 2 may travel about the side of accessory 1 that may be the first to leave the finger, toe, or palm of a user when experiencing sufficient displacement forces. In another exemplary embodiment illustrated by FIG. 4B, harness 2 may have its coupling ends 6A exposed due to a possible inversion in brace 10, in other words, as brace 10 passes through harness 2 section 5, it turns inside out so that inside 11 becomes outside 11 and outside 12 becomes inside 12 of brace 10. Accordingly, an exemplary harness 2 which may be coupled to brace 10 on inside 11 may have its coupling points or ends 6A facing outwardly in the field of vision.

According to the exemplary embodiments of an accessory anchor and accessory anchoring method illustrated in FIGS.

1A-B, 2A-B, 3A-B, and 4A-B, the accessory may be worn or not worn by a user when it is anchored. That is, the anchoring of an exemplary accessory according to an exemplary accessory anchoring method may involve sliding a portion of harness 2 (for example, section 5) underneath accessory 1 (such as a wedding ring) while it is being worn on a digit (for example, on the user's finger, toe, or palm). Exemplary expansion, pass, and loop steps described may be performed without the user ever removing the accessory 1. Whether accessory 1 is worn or not worn during an exemplary accessory anchoring method, after the loop about accessory 1 is complete, an exemplary brace 10 may be configured to attach to the user's arm, wrist, leg, or ankle. Where the user keeps accessory 1 on their finger, toe, or palm during anchoring, brace 10 may be configured to snap, tie, lock, or otherwise attach to the user's arm, wrist, leg, or ankle. According to the exemplary embodiments described herein, a user may swiftly anchor an accessory 1 before wearing the accessory 1 or while accessory 1 is being worn. Additionally, an exemplary accessory anchoring method may be reversed to remove the anchor on an exemplary accessory 1. In one aspect of a reverse anchoring removal step, a user may either expand harness 2 to loosen the loop, remove brace 10 and accessory 1, or remove brace 10 to loosen the loop of harness 2. Other anchor removal methods may be further illustrated and described with reference to the other exemplary embodiments disclosed herein.

Figure 5A:
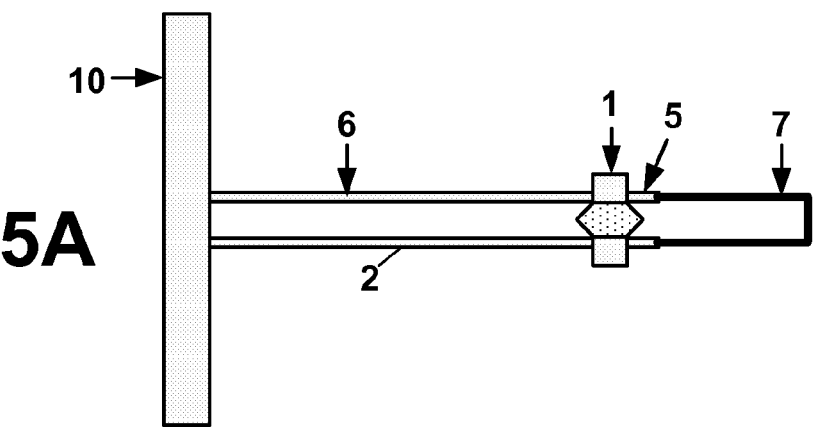
FIG. 5A illustrates an exemplary accessory anchor in an exemplary unwound state.
Figure 5B:
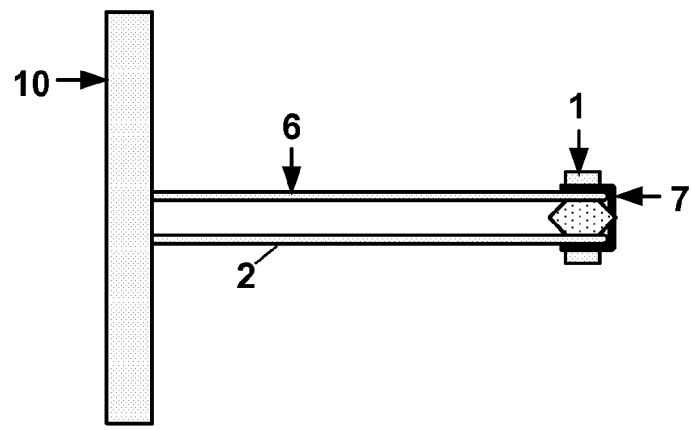
FIG. 5B illustrates an exemplary accessory anchor in an exemplary wound state.

According to the exemplary embodiment illustrated in FIGS. 5A and 5B, an accessory anchor may have a brace 10 with a harness 2 made up of three sections. Section 5 of harness 2 may be the length of harness 2 that passes through accessory 1. Section 6 of harness 2 may be the length of harness 2 coupled to brace 10. Section 7 of harness 2 may be a unique length of harness 2. An exemplary section 7 may be a smaller cross-sectional length of harness 2. Alternatively, section 7 may be made of a different material that may attach to harness 2 section 5 by any of the same coupling methods described for coupling brace 10 and harness 2, for example, flowing through the inside of harness 2 either through section 5 exclusively or sections 5 and 6. According to the aforementioned exemplary alternative, section 7 may be a flexible metal wire traveling within the remainder of harness 2 sections 5 and 6. As a wire, section 7 may beneficially take up less space around the areas of accessory 1 that are in contact with the digit, thereby reducing potential irritation and chafing while also providing sufficient resistance to forces acting on accessory 1. Alternatively, section 7 may be a polymer such as Teflon or ePTFE which may be relatively inert and/or breathable at the interface of accessory 1 and the digit. Further alternatives for section 7 may be polyester, polypropylene, aramids, polyamides, poly-p-phenylene-2, 6-benzobisoxazole (PBO) and any other polymers with substantial tensile strength. As illustrated in FIG. 5B, section 7 may form the substantially arched portion of the harness through which the rest of harness 2 passes.

An exemplary harness 2 section 7 of an exemplary accessory anchor may be one of a number of materials coated by another material, for example, a Nitinol wire covered by ePTFE. According to this exemplary embodiment, section 7 may be configured and coated so as to be smaller in size to fit between an accessory 1 and the digit and to also avoid discomfort while an exemplary accessory anchor is worn. One advantage to a unique section 7 of harness 2 may be to prevent damage to accessory 1 while accessory 1 is anchored in an exemplary anchored mode illustrated in FIG. 5B. For example, section 7 may be made out of silk or Teflon so that it does not scratch a wedding ring 1.

Figure 6A:
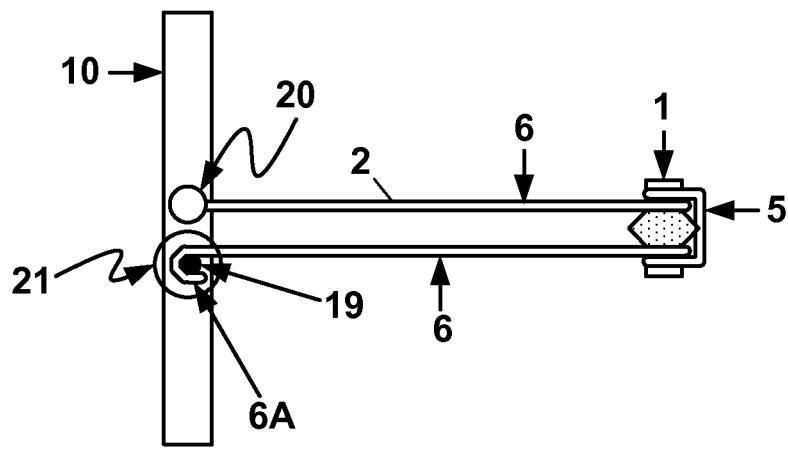
FIGS. 6A and 6B illustrate an exemplary accessory anchor according to additional embodiments of the present invention.

In the exemplary embodiment illustrated by FIG. 6A, a brace 10 may have one or more different coupling mechanisms for coupling harness 2 thereto. For example, brace 10 may have one or more hubs 20 either integrally molded with terminus 6A of harness 2 or holding terminus 6A of harness 2 therewithin. Alternatively, for example, brace 10 may have one or more dials 21 that may rotate pin 19 so as to wrap harness 2 about its peripheral edges to permit adjustment of the length of harness 2. In this alternative exemplary embodiment, terminus 6A of harness 2 may loop around pin 19 and may be coiled about pin 19 upon rotation of dial 21 to shorten the length of harness 2. Otherwise, pin 19 may possess an opening in its cylindrical body for the passage of terminus 6A of harness 2. Subsequent rotation of dial 21 may catch terminus 6A and thereafter cause the rest of section 6 of harness 2 to wind about pin 19 to shorten the length of harness 2. An exemplary hub 20 may be an epoxy mound in which a terminus 6A of harness 2 may be embedded or it may be a combination of plastic slabs glued about terminus 6A. Hub 20 may be integrally molded in brace 10 or may be capable of attaching and detaching from brace 10. For example, hub 20 may be attached to brace 10 by Velcro. Alternatively, hub 20 may be screwed into the surface of brace 10. An exemplary dial 21 may be no larger than a watch winding mechanism or may be considerably larger, depending on the application.

Figure 6B:
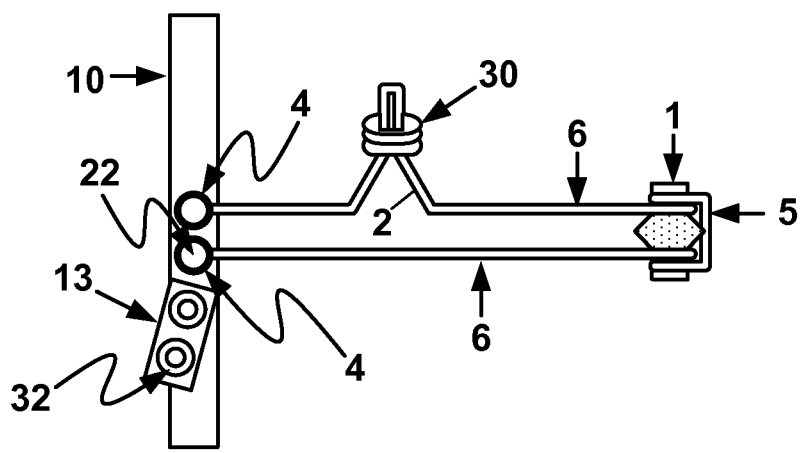

Referring to the exemplary embodiment illustrated in FIG. 6B, a brace 10 may have one or more posts 22 projecting from its surface and one or more post caps 32 coupled to a pliable flap 13 for placement atop the one or more posts 22. According to this exemplary embodiment, harness 2 may have hoop terminus 4 on either end of section 6. An exemplary hoop terminus 4 may be a separate attachment to harness 2 or may be made of the same or similar material as harness 2. While an exemplary hoop terminus 4 may preferably be shaped to be flush with the outermost walls of an exemplary post 22, hoop terminus 4 may be any size or shape, for example a slit in the length of section 6 of harness 2. In an exemplary embodiment where one or more hoop termini 4 engage a corresponding post 22, flap 13 on brace 10 may be placed so that post caps 32 keep either hoop terminus 4 from coming free from around a corresponding post 22. An exemplary post cap 32 and post 22 may be a snap-button combination. Alternative shapes may also be available such as interlocking molded plastic components (of the type found in Lego blocks), or oppositely polarized magnetic wafers. Flap 13 may be integrally attached or molded to brace 10 by any known coupling mechanism known to those skilled in the art, in particular, the methods discussed with relation to coupling harness 2 to brace 10.

The exemplary embodiment of FIG. 6B also illustrates fastener 30 slidingly engaging a section of harness 2. Fastener 30 may be one or more series of rubber rings with elastic rigidity to keep an engaged section of harness 2 from getting loose. An exemplary fastener 30 may be a rubber connector and a metal tightener of the type sold for use in sunglass frame straps, a type of which are sold as Model JP001 part by GoldenEagleJ.com of Kissimee, Fla. Other such tighteners suitable for use in small cross-sectional harness tightening may include bead clamps, rubber ties and other substantial equivalents known to those skilled in the art.

The exemplary embodiments of FIGS. 6A and 6B illustrate exemplary adjustable accessory anchors. Accordingly, an exemplary accessory anchor may have a harness 2 that can be adjusted by one or more of the elements illustrated in FIGS. 6A and 6B to achieve a desired length to accommodate user preferences. For example, accessory anchor may be used to hold a toe ring at the beach but may be used in the evening to hold a wedding ring. According to this exemplary embodiment, the user may use one accessory anchor to accomplish both tasks at different intervals by adjusting the harness 2 to reach the toe ring 1 so that it will be suitably sized for reaching a wedding ring 1 on the user's finger. Thus, an exemplary accessory anchor can anchor accessories located on a foot where the tethering point for the brace will be distally located on the ankle or leg while simultaneously be adjusted to reach an accessory on a user finger across a much smaller distance such as the user's hand, and vice-versa. Alternatively, a user may choose to interchange different harnesses 2 based on the particular brace 10 or need for the harness 2. Flexibility in interchangeability of harness 2 may provide for customizable accessory anchors based on the accessory being anchored. In an exemplary embodiment, users may choose to leave accessories harnessed and merely change braces depending on the circumstances.

Figure 7A:
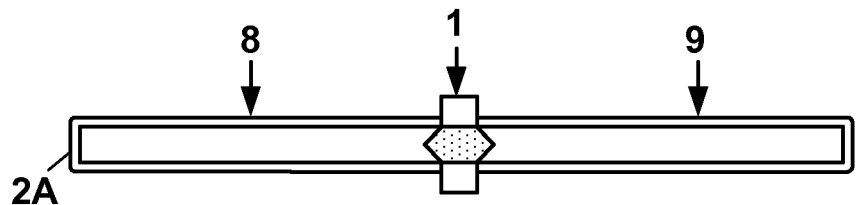
FIG. 7A illustrates another embodiment of an exemplary accessory anchor in an exemplary unwound state.
Figure 7B:
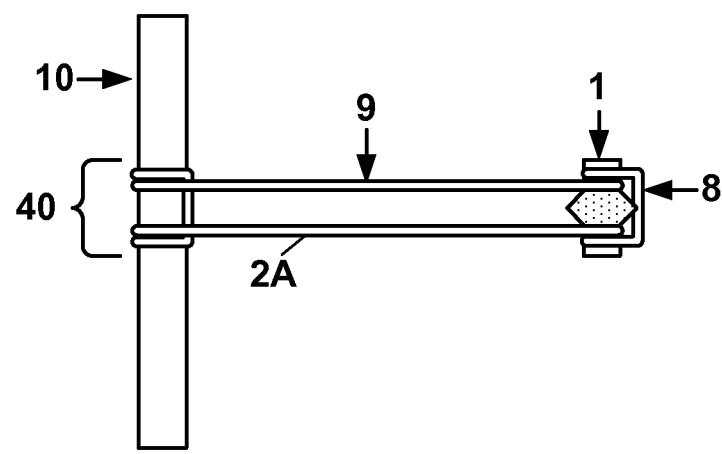
FIGS. 7B and 7C illustrate exemplary wound states for an exemplary accessory anchor.
Figure 7C:
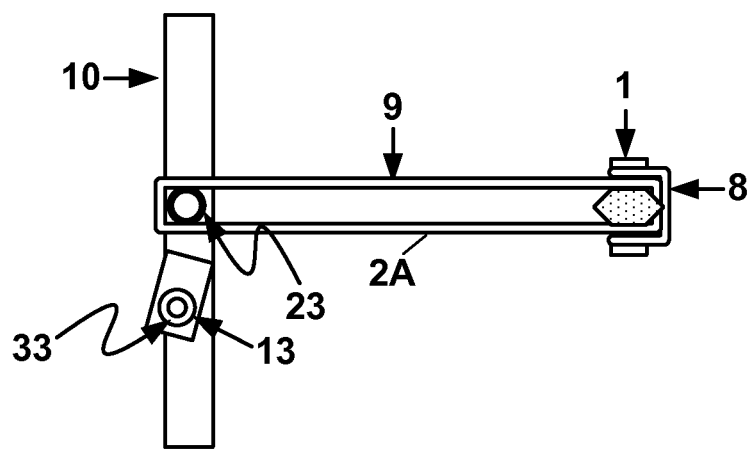

FIG. 7A is an illustrative embodiment of an endless harness 2A, e.g., a harness 2 without a terminus 6A. Instead section 8 of endless harness 2A is the section that loops about accessory 1 and section 9 of endless harness 2A couples to brace 10. FIG. 7B illustrates an exemplary looped mode of an endless harness 2A according to an exemplary embodiment. Like harness 2A with a terminus, accessory 1 is engaged by a length of endless harness (section 8), while the remainder of endless harness (section 9) couples to brace 10. As illustrated in FIG. 7B, an exemplary endless harness 2A may engage brace 10 in the same manner in which it engages accessory 1.

For example, section 9 of endless harness 2A may be placed adjacent inner surface 11 of brace 10 (not shown) or outside surface 12 of brace 10 and expanded according to an exemplary expansion step described with respect to an exemplary harness 2 and brace 10. The remainder of endless harness 2A, such as section 8 with or without an accessory 1 coupled thereto, may proceed to an exemplary passing step whereby the remainder of section 9 and section 8 of endless harness 2A pass through the extended length of section 9. Following an exemplary loop step, endless harness 2A may now be loop-coupled to brace 10 by endless looping 40. As previously stated, an exemplary endless harness 2A may couple to brace 10 as described with or without having coupled to accessory 1 and may or may not be coupled to either brace 10 or accessory 1 while accessory 1 is worn by the user.

Referring to 7C, an exemplary embodiment of an endless harness 2A version of an exemplary accessory anchor may include a post 23 coupled or integrally molded into brace 10. An exemplary accessory anchor may further include a flap 13 with a post cap 33 further disposed or attached to brace 10 for securing endless harness 2A to brace 10. An exemplary post 23 and post cap 33 may be a snap-button arrangement, Velcro, or snap connections similar to the type found in Lego blocks. Flap 13 may be smaller than in cases requiring a plurality of posts due to endless harness 2A's closed structure. In another aspect of this exemplary embodiment, endless harness 2A may be latched into post 23 by wedging it within a receiving portion of the post (a receiving portion shaped like a knitting head of a knitting needle for example) or by looping it through a series of undulations (such as, for example, those in a paper clip).

In FIGS. 8A and 8B, an exemplary embodiment of an accessory anchor may include a piece of clothing 14 worn by the user, such as, for example, a shirt sleeve or pant leg. Alternatively, clothing 14 may be a fabric covering a prosthetic limb. Clothing 14 may act as brace 10 in other embodiments disclosed by coupling endless harness 2A. According to the exemplary embodiment illustrated by FIG. 8A, an endless harness 2A may be clipped, posted, snapped onto or otherwise attached to clothing 14 by a receiver portion 24 and, in certain aspects, a locking portion 34. For example, receiver portion 24 and locking portion 34 may be a snap button arrangement. Alternatively, receiving portion 24 may be a button around which endless harness 2A may be held in place without need of locking portion 34. In another aspect, portion 24 maybe a location for a pin or cuff link depending on the clothing 14. Other substantially equivalent and suitable forms of attachment to clothing 14 may be had with reference to the disclosed embodiments. Flap 15 may be a plastic piece sewed or bonded to clothing 14. For example, flap 15 may hold the cap portion of a snap button in a snap button arrangement between receiver 24 and locking portion 34. Alternatively, flap 15 may be made of the same fabric as clothing 14.

An exemplary double looped endless harness 2A operating with clothing 14 may be illustrated in FIG. 8B. As discussed, section 9 of endless harness 2A may be placed adjacent clothing slit 16 of clothing 14 and expanded according to an exemplary expansion step described with respect to an exemplary harness 2A and brace 10. An exemplary clothing slit 16 may be a slice in the fabric of the clothing worn or it may be premade in the clothing, such as for example the button hole or cuff hole for a dress shirt. For example, endless harness 2A may be placed about the button of a dress shirt cuff before buttoning the cuff about the user's wrist. According to this exemplary embodiment, the user's cuff buttons may act as a brace for harness 2A.

Also, clothing 14 may be made of a mesh fabric or otherwise contain openings to permit passage of an exemplary endless harness 2A therethrough. The remainder of endless harness 2A, such as section 8 with or without an accessory 1 coupled thereto, may proceed to an exemplary passing step whereby the remainder of section 9 and section 8 of endless harness 2A pass through the extended length of section 9. Following an exemplary loop step, endless harness 2A may now be loop-coupled to brace 10 by endless looping 40 about a clothing section 17. As previously stated, an exemplary endless harness 2A may couple to clothing 14 at clothing section 17 as described with or without having coupled to accessory 1 and may or may not be coupled to either brace 10 or accessory 1 while accessory 1 is worn by the user. In another exemplary embodiment according to FIGS. 8A and 8B, clothing 14 may be an ankle warmer, a glove, a sweater, a jacket or form of outerwear, work out clothing, or active wear for hiking, mountain climbing, or bike riding.

Figure 9A:
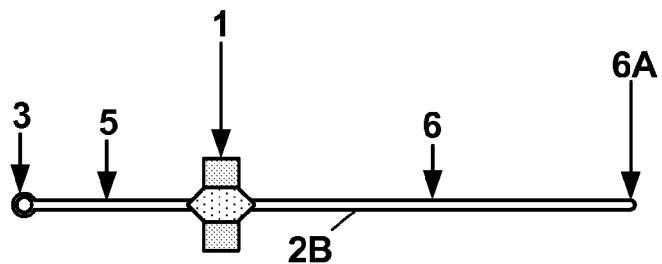
FIGS. 9A, 9B, 9C, and 9D illustrate top plan views of an exemplary accessory anchor in exemplary unwound and wound states.
Figure 9B:
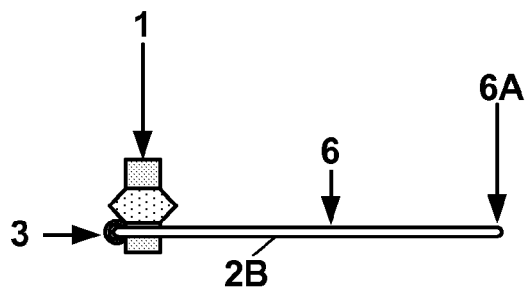

FIG. 9A illustrates an exemplary accessory anchor having a single stranded harness 2B with a section 5 traveling through accessory 1 and a section 6 with a terminus 6A. According to this exemplary embodiment, opposite terminus 6A is hoop 3 coupled to or integrated with section 5 of harness 2B. To engage accessory 1, terminus 6A of harness 2B may pass through hoop 3 and thereby looping about the accessory 1. FIG. 9B is an exemplary embodiment of a looped mode single harness 2B configuration of an exemplary accessory anchor. While terminus 6A may pass over an exemplary accessory 1 to pass through hoop 3 and engage accessory 1, FIG. 9B illustrates an exemplary embodiment where terminus 6A of harness 2B goes underneath accessory 1 to pass through hoop 3 to form the loop at the exemplary looping step for an exemplary accessory anchor. Either mode of operation may be suitable for use in an exemplary accessory anchoring system and method.

Figure 9C:
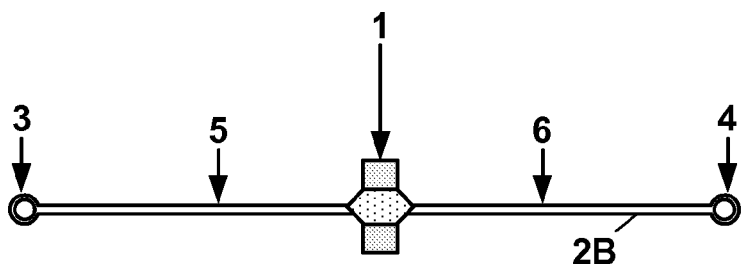
Figure 9D:
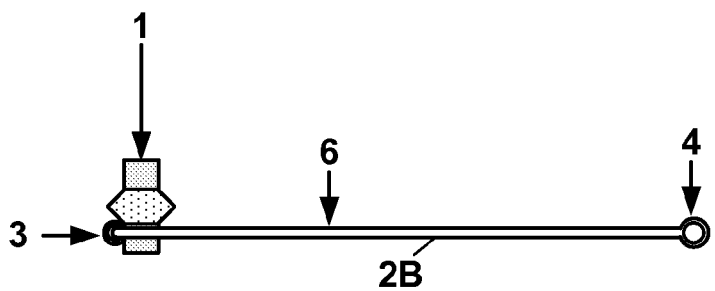

FIG. 9C illustrates an exemplary accessory anchor having a single stranded harness 2B with a section 5 and corresponding hoop 3 traveling through accessory 1 and a section 6 with a corresponding hoop 4. According to the exemplary embodiment illustrated in FIG. 9D, a looped mode of single strand harness 2B is formed from passing hoop 4 of section 6 through hoop 3 of section 5 about accessory 1. While hoop 4 may pass over an exemplary accessory 1 to pass through hoop 3 and engage accessory 1, FIG. 9D illustrates an exemplary embodiment where hoop 4 of harness 2B goes underneath accessory 1 to pass through hoop 3 to form the loop at the exemplary looping step for an exemplary accessory anchor. Either mode of operation may be suitable for use in an exemplary accessory anchoring system and method.

Figure 10A:
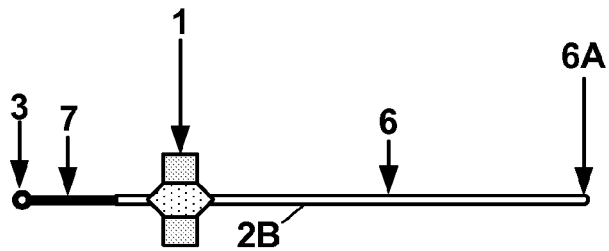
FIGS. 10A, 10B, 10C, and 10D illustrate top plan views of another exemplary accessory anchor in exemplary unwound and wound states.

Referring to FIG. 10A, an exemplary accessory anchor may be made up of a single stranded harness 2B with a section 6 concluding in terminus 6A. Section 7 of harness 2B may pass through accessory 1 or may extend from a portion of section 6 passing through accessory 1. Section 7 concludes in a hoop 3. An exemplary section 7 may be different in constitution and size as compared to the rest of harness 2B. For example, section 7 may be a smaller cross-sectional length of harness 2B. Alternatively, section 7 may be made of a different material that may attach to harness 2B section 6 by any of the same coupling methods described for coupling brace 10 and harness 2. An exemplary section 7 may flow through the inside of harness 2B in whole or in part.

Figure 10B:
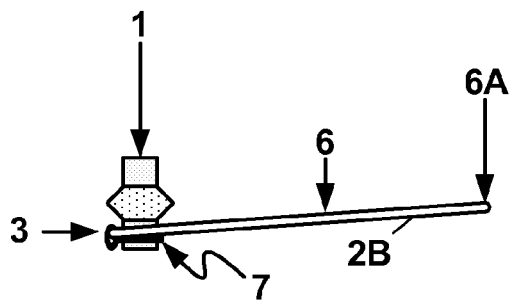

FIG. 10B illustrates an exemplary accessory anchor in a looped configuration. According to this exemplary embodiment, terminus 6A of section 6 of harness 2B may pass through hoop 3 of section 7. In FIG. 10B, an exemplary section 7 engages accessory 1. In an exemplary embodiment, material of harness 2B may be different from material of section 7. For example, harness 2B may be an elastomer while section 7 is a fabric material such as cotton, silk, or nylon. According to this exemplary embodiment, section 7 may be of a material that will avoid tarnishing or harming the aesthetic appearance of accessory 1. Alternatively, section 7 may be a translucent material so as to give an appearance that nothing is attached to accessory 1. While described with respect to the embodiments of FIG. 10B, exemplary section 7 materials of the type described may be applicable in any of the other embodiments disclosed.

Figure 10C:
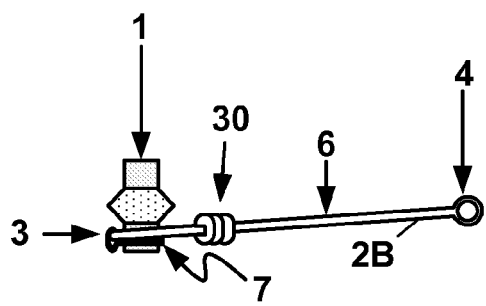

FIG. 10C illustrates an exemplary embodiment of an accessory anchor whereby harness 2B engages an accessory 1 via section 7 through hoop 3. However, rather than have a terminus 6A, harness 2B has a terminal hoop 4. Along the length of harness 2B in the embodiment illustrated by FIG. 10C, a fastener 30 slidingly may engage the portion of accessory 1 most proximal to section 6. According to this exemplary embodiment, fastener 30 may provide additional anchoring support for accessory 1. While fastener 30 may engage accessory 1 on one side and hoop 3 on the other side of an exemplary accessory 1, it may possible for fastener 30 to engage hoop 3 and collectively the combination of hoop 3 and fastener 30 engage accessory 1. According to an exemplary embodiment, fastener 30 may be a rubber tube with a smaller inner diameter than the outer diameter of harness 2B. In this way, fastener 30 may be held in place by friction with pliable harness 2B material until maneuvered into position from an adequate force. Fastener 30 may be able to lock into hoop 3 or slide within open spaces between hoop 3 and section 7. Accordingly, fastener 30 and hoop 3 may increase the anchoring capabilities of each accessory anchor component in a synergistic manner.

Figure 10D:
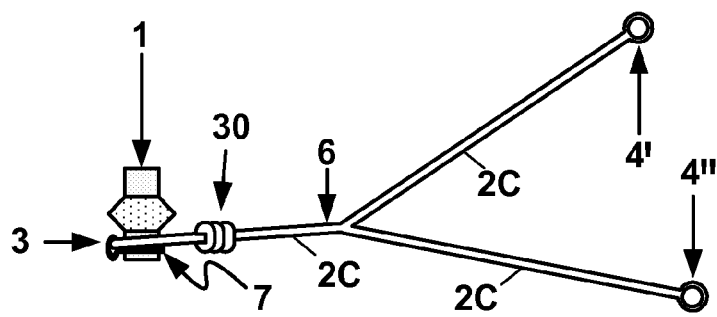

FIG. 10D illustrates a further exemplary embodiment of an accessory anchor. Accessory 1 may be engaged by a harness 2C. Harness 2C has an accessory engaging section 7 terminating in hoop 3, through which the remainder of harness 2C passes to engage accessory 1. However, harness 2C may have a plurality of terminals, as illustrated two are shown, 4' and 4". Thus, section 6 of harness 2C may bifurcate or otherwise split into numerous arms of harness 2c with terminal hoops 4', 4", etc. While illustrated as terminal hoops, it should be understood that an exemplary multiple terminal section 6 may otherwise terminate in termini 6A, 6A', and so on. According to this exemplary embodiment, terminal hoop 4' may connect to a portion of a brace 10 while hoop 4" may connect to the same or a different portion of brace 10. Alternatively hoop 4' may pass through hoop 4" before connecting to brace 10. In yet another alternative, fastener 30 may be used to either engage hoop 3 to assist in engagement of accessory 1 or may be used to engage hoop 4' to ensure the section 6 portion of harness 2C attached to hoop 4" does not recede through hoop 4' while in use.

Figure 11A:
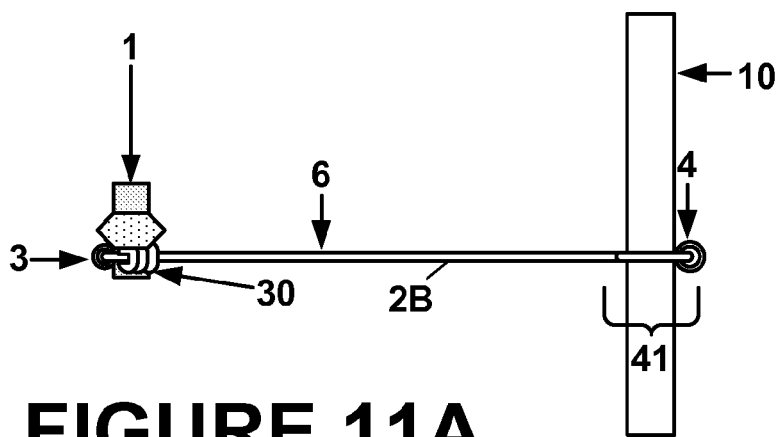
FIGS. 11A and 11B illustrate top plan views of additional exemplary accessory anchors in other exemplary wound states.

Turning now to the exemplary embodiment illustrated in FIG. 11A, a unitary strand harness 2B may be engaged to an accessory 1 as previously described. In addition, harness 2B may be engaged about brace 10 in the same or similar fashion as about accessory 1. According to this exemplary embodiment, a harness 2B may be first engaged about brace 10 by passing elastic hoop 3 of section 6 through hoop 4 of section 6 to engage brace 10 proximal to the hoop 4 terminal of section 6 in a brace engagement 41. Following an exemplary threading step of hoop 3 through accessory 1, hoop 3 may be expanded in an exemplary expansion step to permit passage of engaged brace 10 and hoop 4 of harness 2B therethrough. The resulting exemplary loop step may be illustrated in the illustrative embodiment of FIG. 11A. Alternatively, accessory 1 may be engaged by hoop 3 and section 6 of harness 2B first before engagement of brace 10 in an exemplary passing step through an elastic hoop 4. Either one of or both of the aforementioned embodiments is possible.

Figure 11B:
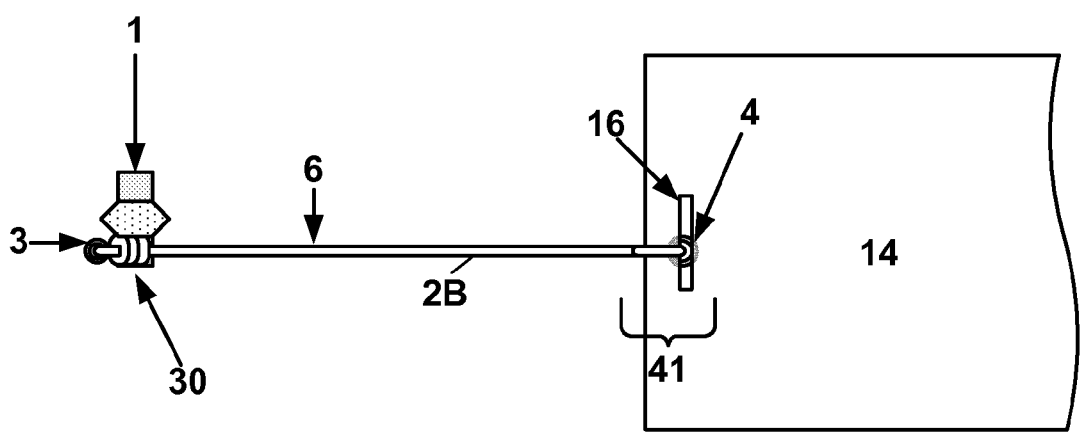

With reference to FIG. 11B, an exemplary harness 2B may be used in an exemplary section of clothing 14 having an exemplary slit 16 and terminal hoop 4 through which harness 2B passes. Clothing engagement 41 may be made through any opening in the clothing material. Further, clothing engagement 41 may be made on a portion of clothing 14 adorning a prosthetic. Fastener 30 may be used to further anchor hoop 3 to accessory 1 or hoop 4 to clothing 14.

Figure 11C:
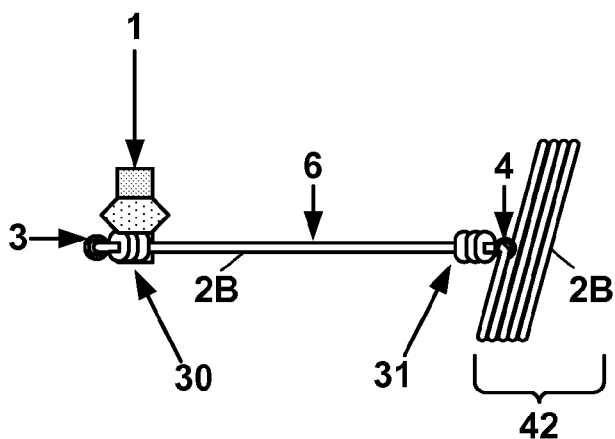
FIG. 11C illustrates a top plan view of an exemplary accessory anchor in further exemplary wound states.

FIG. 11C illustrates strand 2B as a harness and a brace 42. Pursuant to the exemplary embodiment of FIG. 11C, harness 2B may engage accessory 1 through hoop 3. At the location of hoop 4, harness 2B may be wrapped into multiple winding coils 42. One or more coils in an exemplary arrangement according to FIG. 11C may act as a brace 42 as it anchors the remaining un-coiled section 6 of harness 2B to the appendage of a user. In an exemplary embodiment, a strand 2B may be folded so that a middle portion of section 6 may be wrapped about a user's wrist before passing an engaged accessory 1 and hoop 3 through elastically expandable hoop 4 and thereby terminate the brace 42 formed of harness 2B. Accordingly, a strand brace 42 may be customized by a user for any size wrist and for size and comfort. While possible in any of the disclosed embodiments, two separate fasteners 30 slide about section 6 of harness 2B to apply engagement pressure on hoops 3 and 4. An exemplary fastener 30 most proximal to hoop 4 may also have a clip thereon for lockingly engaging hoop 4 so prevent untangling of brace 42.

In a hybrid embodiment, a harness 2C as utilized in the illustrative embodiment in FIG. 10D, may be used according to the harness/brace 2B method for forming harness 2B and brace 42 as illustrated in FIG. 11C. For example, a brace 42 made of harness 2C may be formed while allowing one of the plurality of unattended hoop terminals to engage the hoop terminal most proximal to brace 42. Thus, with three hoops (3, 4', and 4") an exemplary harness-brace 42 may be formed without sacrificing convenience of engaging accessory 1 using other available hoops.

According to an exemplary embodiment, harness 2C would be involved in a thread, pass, and loop step through an expandable hoop 3. As two or more hooped ends (illustrated by 4' and 4") are brought through expandable hoop 3, accessory 1 may become engaged by the loop of harness 2C proximal to hoop 3. The remaining length of harness 2C may be used to form brace 42 about the user or about a prosthetic or article of clothing 14. Where the two or more hoops (e.g., 4' and 4") meet, they may be looped through one another to tighten brace 42. In this way, multiple hoop harnesses such as the exemplary harness 2C of FIG. 11C may advantageously provide further loop-tightening capabilities for which a fastener 30 might otherwise be needed.

An exemplary brace 42 of the type illustrated in FIG. 11C may be re-used in conjunction with a brace 10, a prosthetic, clothing 14, or by itself as a brace 42, depending on the particular needs.

Figure 11D:
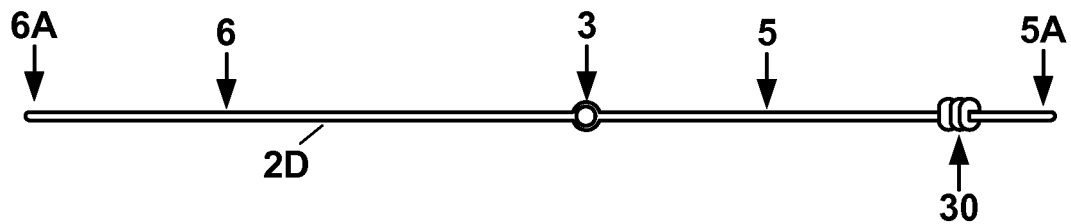
FIGS. 11D and 11E illustrate an alternative exemplary harness for use in the disclosed embodiments.

Referring to FIG. 11D, another exemplary harness 2D may be utilized for any of the aforementioned strand harness embodiments described. An exemplary harness 2D may have a proximal end 6A terminating a proximal section 6. Exemplary harness 2D may have a distal end 5A terminating a distal section 5. Sections 5 and 6 may be separated by one or more hoops 3. In a preferred embodiment, distal section 5 is 75% shorter than proximal section 6. In another preferred embodiment, distal section 5 is between about 82% and 91% shorter than proximal section 6. The exemplary thread, expansion, pass and loop method described for other exemplary harnesses 2B and 2D may be utilized to engage an accessory 1 about section 5 by threading 5A through hoop 3 and thereby looping accessory 1 at the distal section 5. According to one embodiment hoop 3 may not need to be expanded if a removable fastener 30 is used to tighten the passed end 5A of section 5 about accessory 1. Alternatively, hoop 3 may be expandable to allow passage of 5A and fastener 30 through hoop 3's expanded opening and thereafter tighten the engagement about an exemplary accessory 1.

Figure 11E:
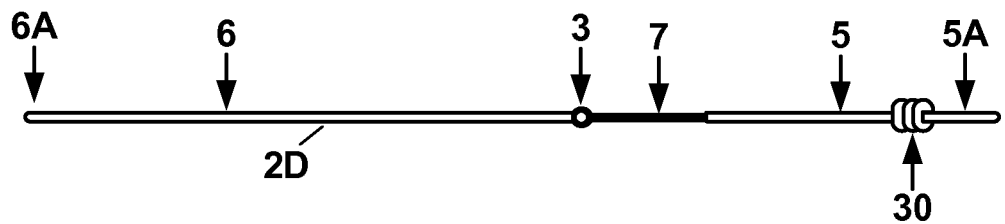

While similar in operation to that of harness 2D in FIG. 11D, an exemplary harness 2D as illustrated in FIG. 11E may be made of a strand of material or materials that are not substantially uniform in cross-section. In one embodiment, a narrower cross-section 7 may be used at the most proximal portion of section 5 to hoop 3. Accordingly, the exemplary engagement methodology for exemplary harnesses 2D as described may also include a narrower section 7 engagement to reduce material engaging accessory 1. In an exemplary embodiment, cross-section 7 may be Teflon, ePTFE, silk, Nitinol, or other thin, durable materials suitable for the purposes of an accessory anchor as described.

Figure 11F:
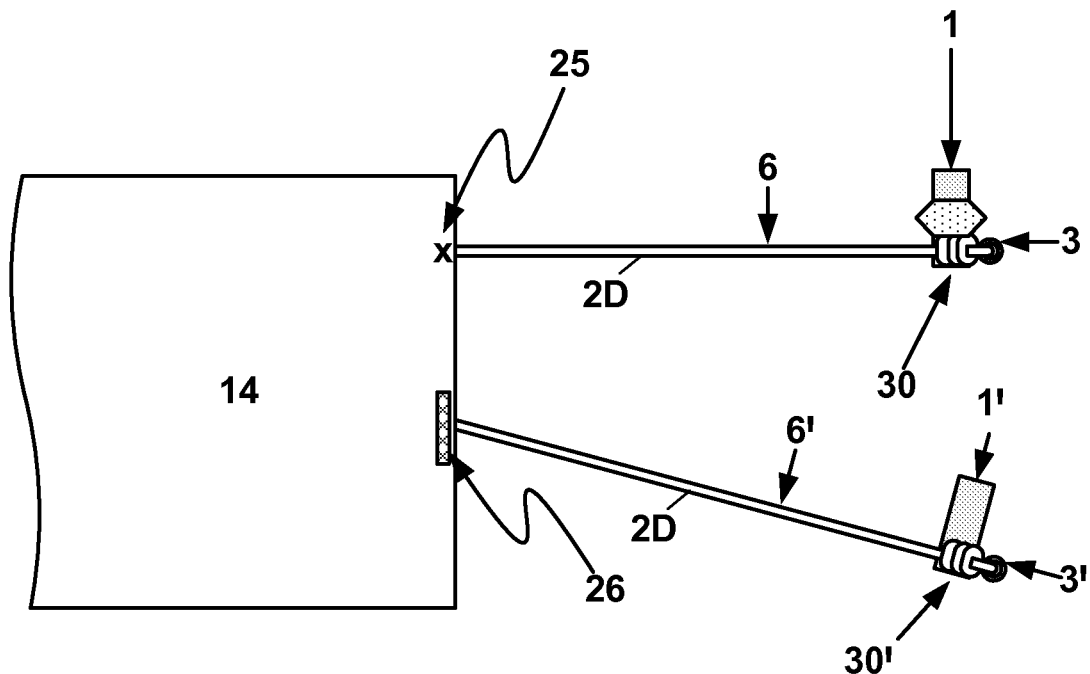
FIG. 11F illustrates a top plan view of an exemplary accessory anchor in further exemplary wound states.

Referring to FIG. 11F, a proximal end 6A of an exemplary harness 2D may be coupled to clothing 14 by numerous means to allow for operative attachment of an exemplary accessory 1 according to any of the embodiments related to FIGS. 11D and 11E as described. For example, proximal end 6A may be coupled to clothing 14 by a stitching 25, which may include one or more types of stiches known to those skilled in the art. An exemplary stitch may be a cross stitch, straight stitch, button hole, chain, running or zigzag, or any other suitable stitch to hold proximal end 6A to clothing 14. Alternatively, proximal end 6A may be coupled to clothing 14 by one or more adhesive 26 which may include glue, epoxy, weld, solder, melt bond, or other suitable adhesive connection. While not illustrated, an exemplary coupling mechanism may be to knot section 6 and its proximal end 6A about an opening in clothing 14 (such as the exemplary slot 16 in clothing 14 shown in FIGS. 8B and 11B). Another further alternative for coupling proximal end 6A of an exemplary harness 2D to clothing 14 may be through one or more connection mechanisms.

According to another exemplary embodiment of FIG. 11F, more than one exemplary harness 2D may be coupled to clothing 14 according to one or more of the connection mechanisms described. In an exemplary embodiment, section 6 of a harness 2D may be stitched to clothing 14. For example, harness 2D section 6 may be coupled to clothing 14 by a cross stitch 25. A second harness 2D section 6' may be coupled to clothing 14 by an adhesive 26. According to this exemplary embodiment, a second harness 2D may be used to couple additional accessories 1' and loops 3' with the option for one or more fasteners 30'. In a preferred embodiment, a shirt sleeve 14 may have two strands 2D for coupling a first ring 1 and a wedding ring 1' to the middle finger and ring finger, respectively, of an individual. According to the operation described, the user can wear the shirt with both strands 2D can use it when wearing such ring 1 and wedding ring 1'. In another preferred embodiment, the pant leg 14 of a pair of jeans may have two strands 2D to couple toe rings 1 and 1' to a user's foot for summer wear. Any other form of clothing 14 may be suitable for coupling one or more strands 2D for use as an anchor accessory.

Figure 12A:
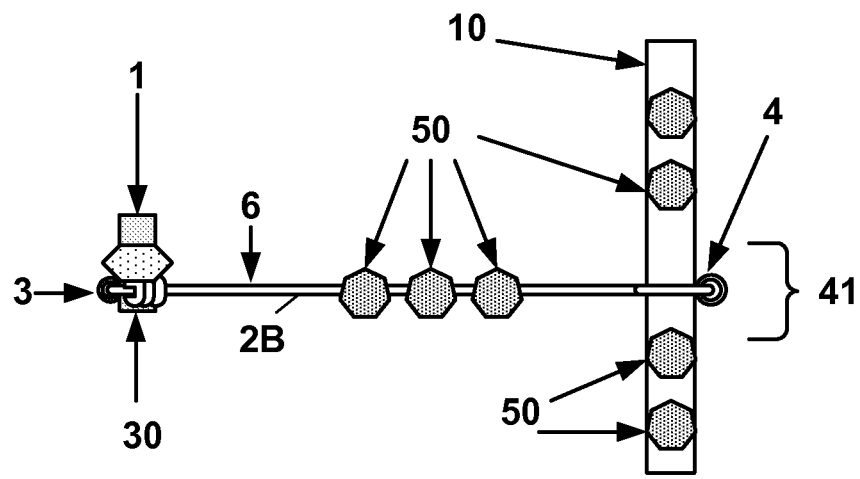
FIGS. 12A and 12B illustrate a top plan view of an exemplary accessory anchor with charms in exemplary wound states.
Figure 12B:
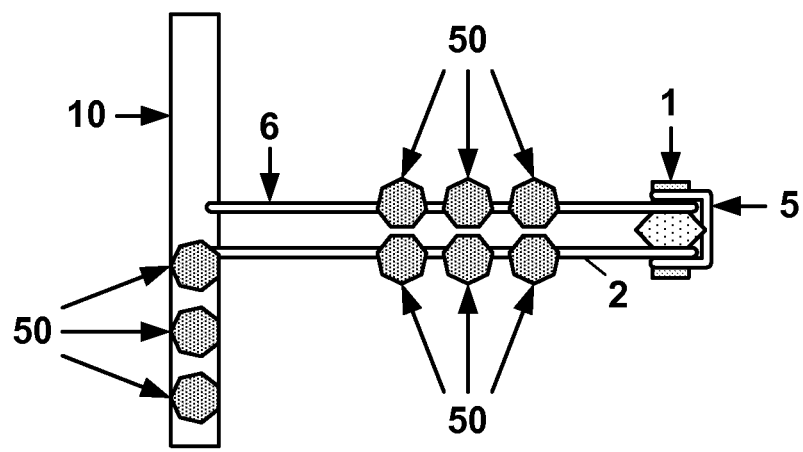

Referring to the exemplary embodiment of FIG. 12A, an exemplary harness 2B may be coupled to a brace 10 with one or more of harness 2B and brace 10 covered in one or more charms 50. Charm 50 may be any form of jewelry known to those skilled in the art, including glitter, prints, styled threads, ribbons, glass, plastics, gem stones, crystals, sequins, beads, rhinestones, pearls, diamonds, or any other object with aesthetic appeal known to those skilled in the art. As shown in FIG. 12A, a charm 50 may be glued, welded, sewed to, knotted, or otherwise adhered to harness 2B about section 6 or on outer surface 12 of brace 10. In FIG. 12B, charm 50 may be attached to the harness 2 or brace 10 as shown in other exemplary embodiments. While the illustrative embodiments of FIGS. 12A and 12B illustrate charms 50 on sections 6 of harness 2 and 2B, charm 50 may be placed on any location of an exemplary harness 2, 2A, 2B, 2C and 2D in suitable position for operation of these harnesses in the described embodiments. Thus, while harnesses 2 and 2B are illustrated with charms, the exemplary embodiment of FIGS. 12A and 12B may apply to any of the other harnesses 2, 2A, 2B, 2C and 2D described. As illustrated, these exemplary embodiments contain additional features for an exemplary accessory anchor system.

Figure 13A:
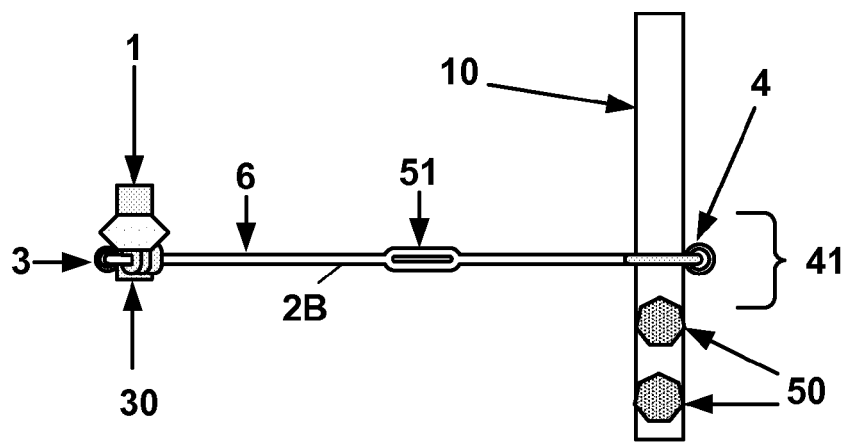
FIGS. 13A, 13B, and 13C illustrate top plan views of an exemplary accessory anchor configured for exemplary accessories in exemplary wound states.

FIG. 13A illustrates an exemplary harness 2B with a harness opening 51 for reception of one or more charms 50 therein. As illustrated in FIG. 13A, harness opening is preferably found on section 6 of harness 2B, but may also be found in section 5 of an exemplary harness. Optionally, a harness 2B with harness opening 51 may be engaged to brace 10 with charms 50 via brace engagement 41. An exemplary harness opening 51 may be the same size or larger than hoops 3 and 4. Alternatively, harness opening 51 may be large enough to preclude displacement of fastener 30. As illustrated, this exemplary embodiment is an additional feature of an exemplary accessory anchor system.

Figure 13B:
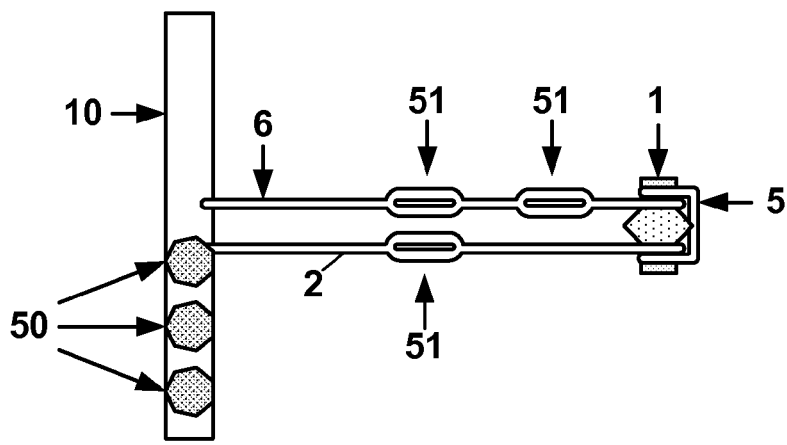

FIG. 13B illustrates an exemplary harness 2 with numerous harness openings 51 in section 6. While harness 2 may have harness openings 51 spaced anywhere about its length, it may have certain harness openings 51 aligned with one another on either strand of looped harness 2. This exemplary embodiment is not limited to just loop harness 2 but may also apply to endless loop harness 2A. As illustrated, this exemplary embodiment is an additional feature of an exemplary accessory anchor system.

Figure 13C:
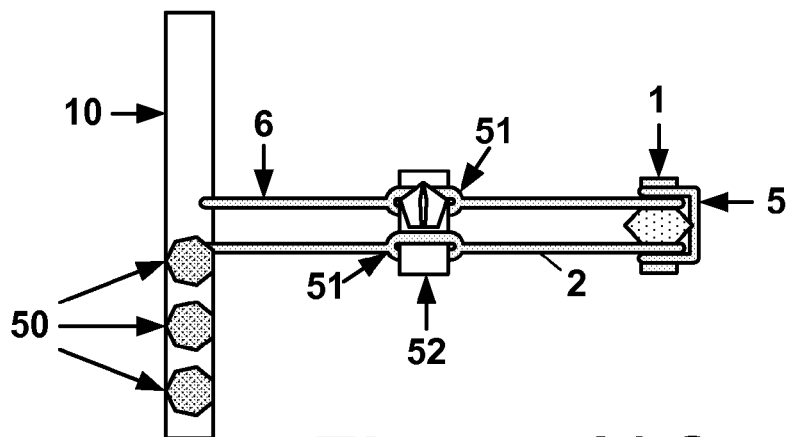

In the illustrative embodiment of FIG. 13C, a charm 51 may be attached to harness 2 through one or more of harness openings 51. As shown, charm 51 may be like any other charm 50 described, or may be another suitable charm according to those skilled in the art. Charm 51 may be coupled by glue, melt bond, die casting, or any other suitable form of attachment mechanism to insert 52. Insert 52 may slide within harness openings 51, clip to one or more harness openings 51, or provide frictional or clamping forces to lodge harness openings 51 onto its surface. In a preferred embodiment, a medallion 51 may be held in place on a broche 52 that contains edging that would beheld securely inside the harness openings 51 of an exemplary harness 2 or 2A when coupled to an exemplary brace 10 or clothing 14 acting as part of an exemplary accessory anchor.

Figure 14:
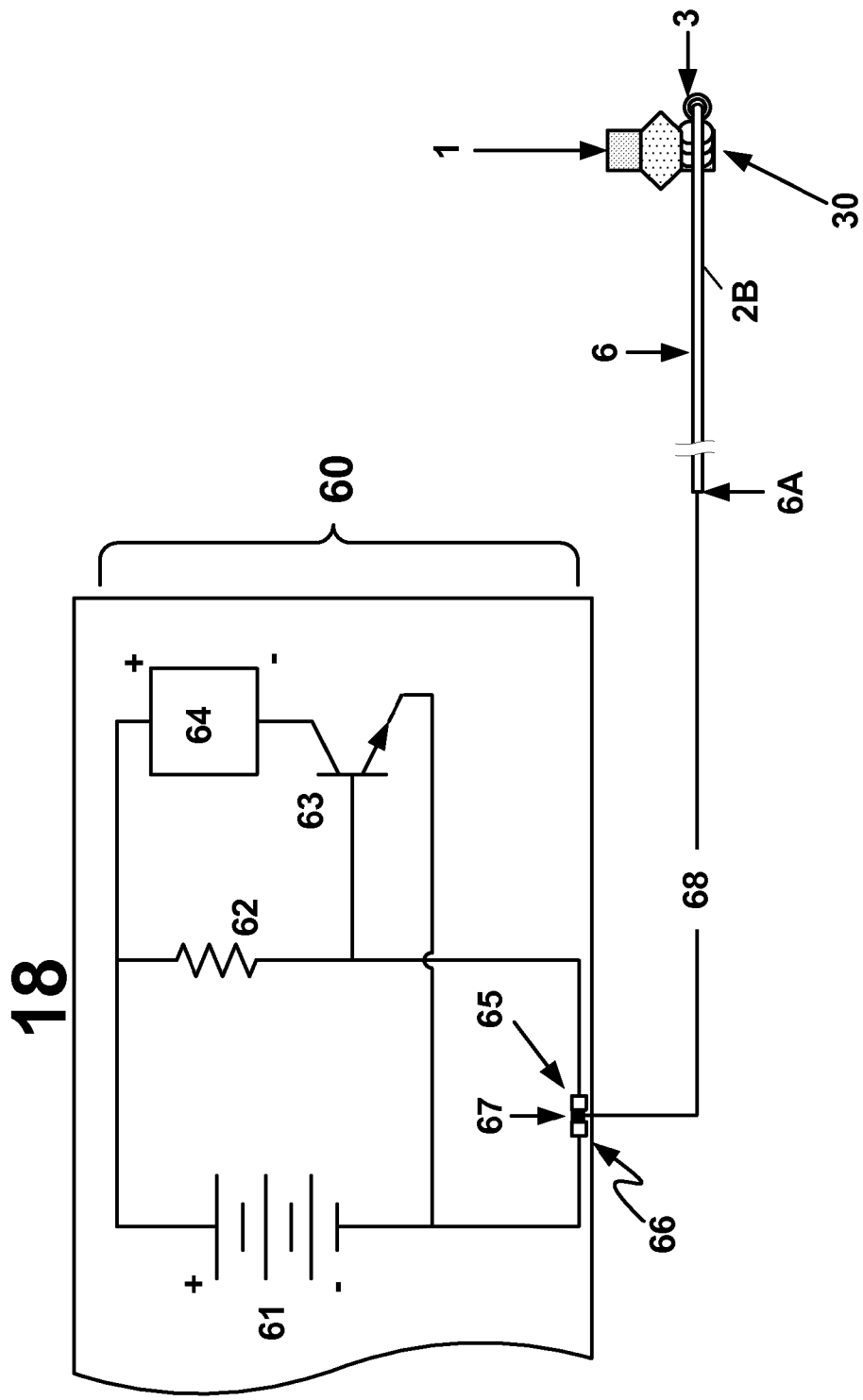
FIGS. 14 and 15 illustrate an exemplary accessory anchor circuit.

FIG. 14 illustrates another exemplary embodiment of the accessory anchor described. In FIG. 14, a brace 18 may contain a circuit 60 for detecting and signaling a disconnection of harness 2, 2A, 2B, 2C, or 2D with brace 18. Brace 18 may be the same as or similar to brace 10 in material, size and composition, or may be a type of clothing 14 or prosthetic. Circuit 60 contains a battery 61 coupled to a resistor 62, a suitable transistor 63 and a signal device 64. Battery 61 is also connected to junctions 65 and 66. In an exemplary embodiment, battery 61 creates voltage in circuit 60 to drive current through resistor 62 so long as junctions 65 and 66 are connected via contact 67. During this exemplary operation, circuit 60 may preclude current going through transistor 63 and prevent signal device 64 from operation. Contact 67 may be tethered to the proximal end 6A of section 6 of an exemplary harness 2B of an exemplary accessory anchor via lead 68. Lead 68 may be a conductor of electricity running in or alongside a surface of an exemplary harness 2B Like section 7 of exemplary harnesses described, lead 68 may be contained within harness 2, 2A, 2B, 2C, or 2D. Alternatively, section 7 may be the same material as lead 68. Contact 67 may be coupled to lead 68 by glue, soldering, welding, or by being part of the same connective material. In a preferred embodiment, lead 68 may be made of the same material as an exemplary section 7 but then be epoxied to contact 67. While contact 67 may be coupled to harness 2B, any harness described may be utilized in conjunction with brace 18 and circuit 60 as an exemplary accessory anchor.

Contact 67 may be suitably sized to fit between junctions 65 and 66 of circuit 60. Contact 67 is preferably a conductor of electricity to maintain electrical contact with junctions 65 and 66; however, contact 67 may be coupled to a conductor to maintain continuity of circuit 60 even though it may not itself be a conductor. The interaction of junctions 65 and 66 and contact 67 may be further illustrated in FIG. 16. While circuit 60 is not broken at the portion of the circuit containing junction 65, contact 67, and junction 66, no current should be provided through transistor 63 to signal device 64. In an exemplary embodiment, a closed circuit 60 does not allow current from battery 61 to turn on signal device 64.

In a preferred embodiment, battery 61 may be made up of two in-series 2.0 V Lithium micro-batteries from Seiko Instruments Inc. Resistor 62 may be a 10-1000 kΩ resistor. Transistor 63 may be a 2N4401 NPN switching transistor, however a 2N5179 or 2N222 NPN switching transistors may also be suitable. A preferred signal device 64 may be a 1.5-3.5V magnetic or piezoelectric DC buzzer, such as a Series B814 magnetic buzzer from Philmore-Datak of Rochester, N.Y. An alternative preferred device 64 may be one or more LEDs.

Figure 15:
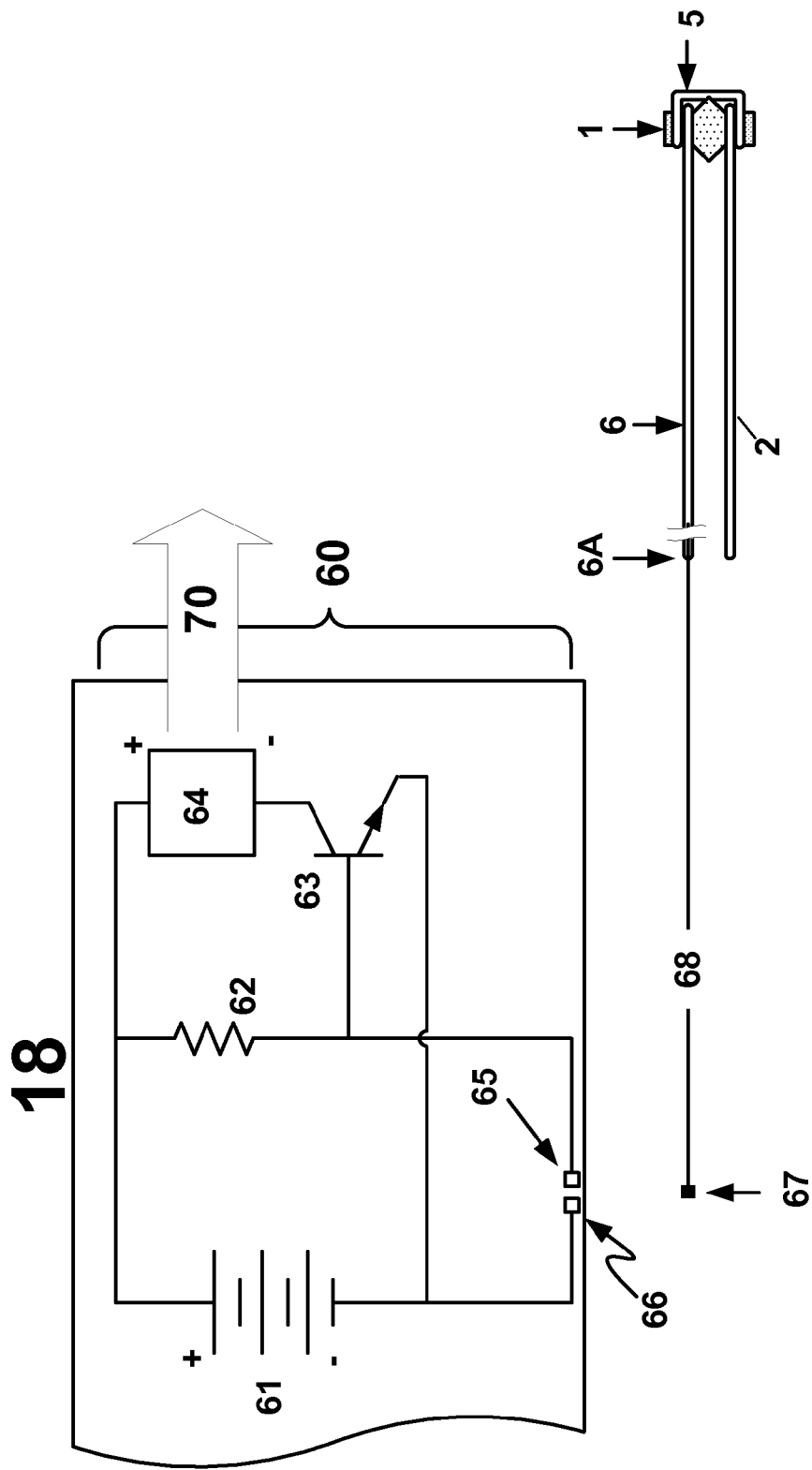

In FIG. 15, the circuit 60 of brace 18 may activate signal device 64 to produce a signal 70 to the user when contact 67 of an exemplary harness 2 becomes disconnected from circuit 60 junctions 65 and 66. According to the illustrative embodiment of FIG. 15, when current cannot pass from junction 66 to junction 65, battery 61 may provide current through signal device 64 and transistor 63 creating a voltage drop across signal device 64 to activate it. Signal device 64 may provide one or more types of signals to a user, such as a vibration, a sound, or an illumination from one or more LEDs. In an exemplary accessory anchor, a brace 18 containing a circuit 60 may alert a user that an accessory 1 is no longer anchored to brace 18. While circuit 60 may be implemented as an exemplary signaling circuit, persons of ordinary skill in the art may realize other suitable equivalent circuits for alarming users to the disconnection of an exemplary harness 2, 2A, 2B, 2C, and 2D from a brace 18.

Figure 16:
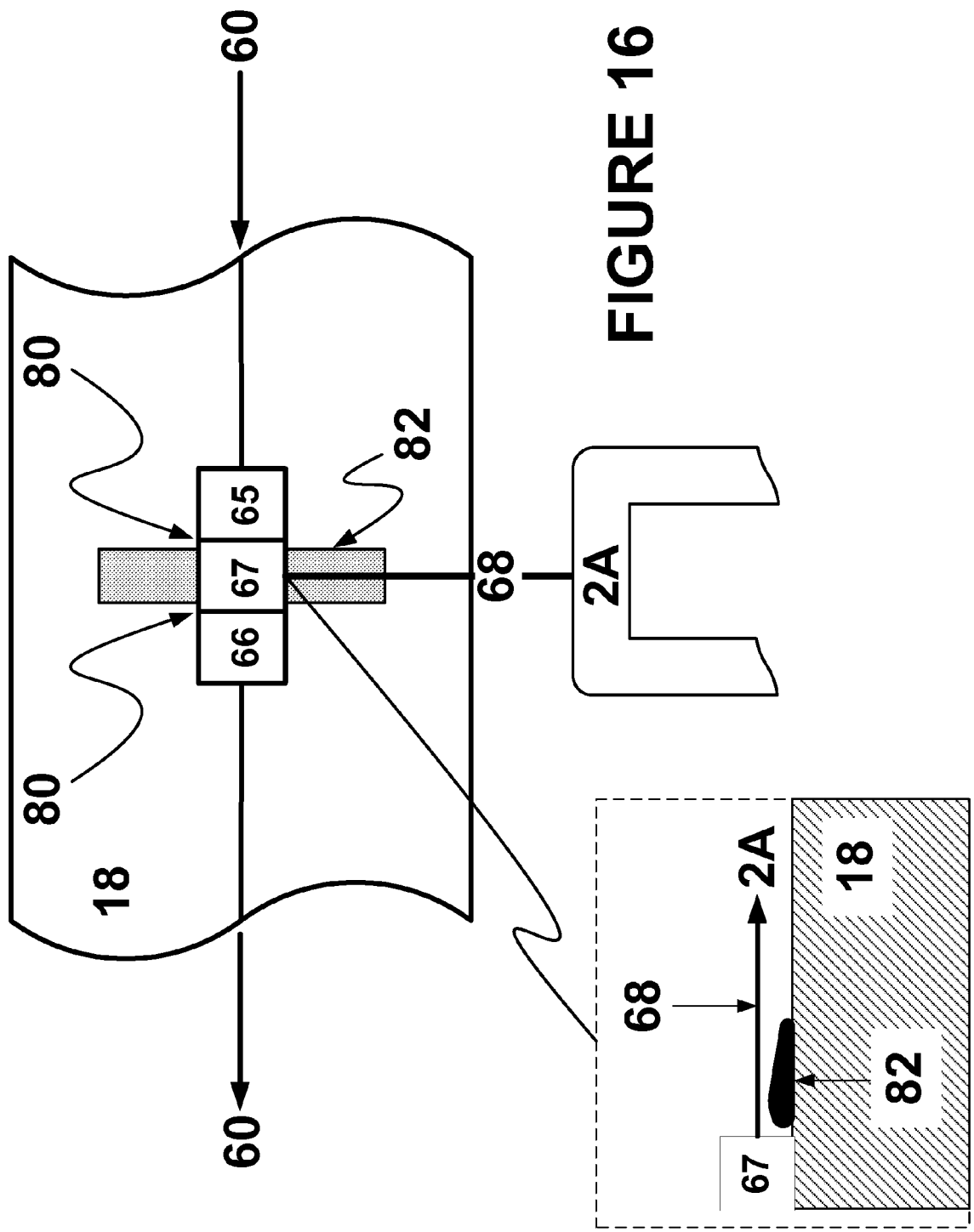
FIG. 16 illustrate an exemplary subsection of an exemplary accessory anchor circuit.

FIG. 16 illustrates an exemplary section of circuit 60 showing junctions 65 and 66 and contact 67. Contact 67 is illustrated tethered by lead 68 to an exemplary endless loop harness 2A, although any harness 2, 2A, 2B, 2C, or 2D may be coupled to a circuit 60. In an exemplary embodiment, contact 67 may be frictionally coupled to junctions 65 and 66 by friction edges 80. An exemplary friction edge may be a roughened or corrugated conductive face capable of withstanding a certain amount of frictional force before allowing contact 67 to disengage. Alternatively, edges 80 may be angled walls with complementary walls of contact 67 abutting thereto. In this alternative embodiment, displacement of harness 2A tethered to contact 67 may cause deformation in junctions 65 and 66 that would require re-configuration of the junctions of circuit 60 before reconnecting harness 2A to brace 18 circuit 60.

However, other configurations of contact 67 and junctions 65 and 66 may allow for reconnection of contact 67 in brace 18 after departure of harness 2A from brace 18. An exemplary reconnection configuration, may involve a rubber surface 82 which prevents sliding displacement of contact 67. Surface 82 may be configured so that the frictional force exerted on contact 67 is sufficient to withstand moderate or strong tensions on lead 68. Accordingly, a suitable surface 82 may prevent contact 67 from disengaging from circuit 60 up to a certain force limit. Surface 82 may also consist of rubber hurdles or speed bumps over which an exemplary contact 67 may not overcome unless a certain amount of tension on lead 68 is met.

For example, FIG. 16 shows a more detailed view of an exemplary contact 67 on surface of brace 18 with an exemplary speed-bump style surface 82 which would preclude departure of contact 67 in a direction tending towards displacement of harness 2A. According to this exemplary embodiment, the surface opposite the direction of harness 2A displacement may have a relatively steep incline. However, to replace a disengaged contact 67 back within brace 18, the less steep incline on the side facing towards harness 2A of surface 82 may allow easier replacement of contact 67 back within brace 18 and complete circuit 60. While FIG. 16 illustrates the use of an exemplary accessory anchor harness 2A, the disclosed embodiments related thereto may involve any contact 67, edge 80 or harness 2, 2A, 2B, 2C, or 2D described.

Embodiments of exemplary accessory anchors which utilize circuits 60 in their braces 18 may be useful where users would want notification of a disengaged or detached accessory 1. Alternatively, an exemplary circuit 60 may be optional.

As disclosed, any of the various braces 10/18, clothing 14, harnesses 2, 2A, 2B, 2C, and 2D, and their various ends, sections and components may be interchangeable to achieve the objectives of an exemplary accessory anchor system using exemplary accessory anchoring methods.

Many further variations and modifications may suggest themselves to those skilled in art upon making reference to above disclosure and foregoing illustrative embodiments, which are given by way of example only, and are not intended to limit the scope and spirit of the interrelated embodiments of the invention described herein.

The invention claimed is:

1. A human digit accessory anchoring system, comprising:
an annular brace configured to be worn on a human limb;
a human digit accessory; and
a harness comprising:
a pair of non-overlapping portions passable around the human digit accessory; and
a substantially arched portion through which the non-overlapping portions pass to couple the human digit accessory to the brace,
wherein the substantially arched portion of the harness has a first cross section and each of the pair of non-overlapping portions has a second cross section, wherein the first cross section is smaller than the second cross section.

2. The human digit accessory anchoring system of claim 1, wherein the first cross section is a circular cross section.

3. The human digit accessory anchoring system of claim 1, wherein the harness is integral with the brace.

4. The human digit accessory anchoring system of claim 1, wherein the brace comprises a material selected from the group consisting of fabrics and metals.

5. The human digit accessory anchoring system of claim 4, wherein the fabric is a breathable material.

6. The human digit accessory anchoring system of claim 5, wherein at least one of the materials comprises ePTFE.

7. The human digit accessory anchoring system of claim 5, wherein the brace comprises a material selected from the group consisting of fabrics and metals.

8. The human digit accessory anchoring system of claim 4, wherein the harness is permanently coupled with the brace.

9. The human digit accessory anchoring system of claim 1, wherein the first cross section and second cross section are made up of different materials.

10. The human digit accessory anchoring system of claim 1, wherein the harness is permanently coupled with the brace.

11. The human digit accessory anchoring system of claim 10, wherein the second cross section is permanently coupled with the brace.

12. A human digit accessory anchoring method, comprising the steps of:
threading a harness about a human digit accessory configured to be worn on a human digit so that the human digit accessory lies between two portions of the harness each of which has a different cross-section;
passing a brace configured to be about a human limb through the harness; and
passing at least two non-overlapping portions of the harness around the human digit accessory and through a substantially arched portion of the harness.

13. The human digit accessory anchoring method of claim 12, wherein the step of threading the harness about the accessory takes place while the human digit accessory is not about the human digit.

14. The human digit accessory anchoring method of claim 13, further comprising the step of coupling the brace to the human limb while the human digit accessory is not about the human digit.

15. The human digit accessory anchoring method of claim 12, wherein the substantially arched portion of the harness has a different cross-section from at least one other portion of the harness located proximal to the human digit accessory.

16. The human digit accessory anchoring method of claim 15, wherein the substantially arched portion of the harness and the at least one other portion of the harness comprise different materials.

17. The human digit accessory anchoring method of claim 15, wherein the fabric is breathable.

18. The human digit accessory anchoring method of claim 17, wherein the material of the substantially arched portion is breathable.

19. The human digit accessory anchoring method of claim 18, wherein the brace comprises a material selected from the group consisting of fabrics and metals.

20. The human digit accessory anchoring method of claim 12, wherein the brace comprises a material selected from the group consisting of fabrics and metals.

* * * * *